US 8,731,956 B2

(12) United States Patent
Bejjani et al.

(10) Patent No.: US 8,731,956 B2
(45) Date of Patent: May 20, 2014

(54) WEB-BASED GENETICS ANALYSIS

(75) Inventors: Bassem A. Bejjani, Spokane, WA (US);
Lisa G. Shaffer, Colbert, WA (US);
Blake Ballif, Greenacres, WA (US);
Brice Tebbs, Spokane, WA (US); Kyle Sundin, Spokane, WA (US)

(73) Assignee: Signature Genomic Laboratories, Spokane, WA (US)

( * ) Notice: Subject to any disclaimer, the term of this patent is extended or adjusted under 35 U.S.C. 154(b) by 482 days.

(21) Appl. No.: 12/265,396

(22) Filed: Nov. 5, 2008

(65) Prior Publication Data

US 2010/0115421 A1  May 6, 2010

Related U.S. Application Data

(60) Provisional application No. 61/038,623, filed on Mar. 21, 2008.

(51) Int. Cl.
*G06Q 10/00* (2012.01)
*G06F 19/00* (2011.01)
*G06F 15/16* (2006.01)
*G06F 3/00* (2006.01)
*G06F 17/30* (2006.01)

(52) U.S. Cl.
USPC .................................... 705/2; 702/19; 702/20

(58) Field of Classification Search
USPC ............................................................ 705/2
See application file for complete search history.

(56) References Cited

U.S. PATENT DOCUMENTS

| | | | |
|---|---|---|---|
| 2002/0048763 A1 | 4/2002 | Penn et al. | |
| 2002/0052761 A1 | 5/2002 | Fey et al. | |
| 2002/0177137 A1 | 11/2002 | Hodge | |
| 2002/0183936 A1 | 12/2002 | Kulp et al. | |
| 2003/0003478 A1* | 1/2003 | Depinho et al. | 435/6 |
| 2003/0009295 A1 | 1/2003 | Markowitz et al. | |
| 2003/0220820 A1* | 11/2003 | Sears et al. | 705/3 |
| 2005/0066276 A1 | 3/2005 | Moore et al. | |
| 2005/0074795 A1 | 4/2005 | Hoffman et al. | |
| 2006/0218182 A1 | 9/2006 | Giffard et al. | |
| 2008/0270041 A1* | 10/2008 | Sproles et al. | 702/20 |
| 2010/0094562 A1 | 4/2010 | Shohat | |
| 2010/0115421 A1 | 5/2010 | Bejjani et al. | |
| 2010/0281401 A1 | 11/2010 | Tebbs et al. | |

FOREIGN PATENT DOCUMENTS

WO  WO2010054284(A1)  5/2010

OTHER PUBLICATIONS

Edgar, Robert C., "Muscle: Multiple Sequence Alignment with High Accuracy and High Throughput", Nucleic Acids Research, Mar. 19, 2004, vol. 32, No. 5, pp. 1792-1797.

Ludwig, Wolfgang, et al., "ARB: A Software Environment for Sequence Data", Nucleic Acids Research, Feb. 25, 2004, vol. 32, No. 4, pp. 1363-1371.

(Continued)

*Primary Examiner* — Hiep V Nguyen
(74) *Attorney, Agent, or Firm* — Lee & Hayes, PLLC; Benjamin A. Keim; Brett L. Nelson

(57) ABSTRACT

Techniques for allowing doctors and clinicians to upload genetic data associated with patients for comparison with previously-uploaded genetic data associated with other patients are described herein. These techniques may also allow doctors and clinicians to create notations associated with uploaded patient data. Both the previously-uploaded data as well as the created notations may be used by doctors and clinicians in attempting to diagnosis patients. That is, these techniques allow previously-acquired knowledge to be widely shared for the future benefit in attempting to detect genetic syndromes.

53 Claims, 24 Drawing Sheets

(56) References Cited

OTHER PUBLICATIONS

PCT Search Report for PCT Application No. PCT/US09/63683, mailed Dec. 30, 2009 (5 pages).
CytoSure—lab set up "CytoSure", <<http://www.ogt.co.uk/products_cytosure-dt4.htm>>, retrieved on Jun. 30, 2009, 1 page.
Ensembl Genome Browser "e!Ensembl", <<http://www.ensembl.org/index.html>> retrived on Jun. 30, 2009, 2 pages.
Entrez Genome View "NCBI Map Viewer", <<http://www.ncbi.nlm.nih.gov/projects/mapview/map_search.cgi? taxid=9606>> retrieved on Jun. 30, 2009, NCBI, 2 pages.
UCSC Geonome Browser Home "UCSC Genome Bioinformatics", <<http://genome.ucsc.edu/>> retrieved on Jun. 30, 2009, 3 pages.
Non-Final Office for U.S. Appl. No. 12/614,009, mailed on Oct. 26, 2011, Brice Tebbs, "Interactive Genome Browser", 12 pages.
Non-Final Office for U.S. Appl. No. 12/613,978, mailed on Nov. 6, 2012, Brice Tebbs et al., "Interactive Genome Browser", 11 pages.
Final Office for U.S. Appl. No. 12/614,009, mailed on Apr. 11, 2013, Brice Tebbs et al., "Interactive Genome Browser", 13 pages.
Final Office for U.S. Appl. No. 12/613,978, mailed on May 24, 2013, Brice Tebbs et al., "Interactive Genome Browser", 14 pages.
Final Office for U.S. Appl. No. 12/614,009, mailed on Feb. 2, 2012, Brice Tebbs et al., "Interactive Genome Browser", 13 pages.
Final Office for U.S. Appl. No. 12/614,009, mailed on Aug. 20, 2013, Brice Tebbs, "Interactive Genome Browser", 14 pages.
Australian Office Action mailed Jan. 20, 2014 for Australian patent application No. 2009313292, a counterpart foreign application of U.S. Appl. No. 12/613,978, 3 pages.
Office Action for U.S. Appl. No. 12/614,009, mailed on Jan. 10, 2014, Brice Tebbs, "Interactive Genome Browser", 13 pages.
Voight, "Approaching Human Genetics from a Population-Based Paradigm", Order No. 3219598, The University of Chicago, Ann Arbor: ProQuest Web Mar 17, 2014, 2006, 190 pages [in U.S. Appl. No. 12/614,009 on Mar. 26, 2014].

* cited by examiner

400

Genetic Analysis Application

← → ✕ ↻ 🏠 🔍 Search ☆ http://www.site.com/Sign_on_page

Sign On Page

Service Provider 124 is the leader in microarray testing of individuals suspected to have chromosome abnormalities, and introduces the next level of laboratory support: Genetic Analysis Application 128.

Supported by the same proprietary software in our laboratory, this service allows complete hands-on analysis and interpretation of test results generated using our microarray technology. With this service, users may view test results online and sign out cases processed at our laboratory. This service also allows access to a secure online server to visualize microarray test results, browse the genome databases and order BAC clones used on our chips for FISH testing. Use our vast experience to enhance your work. And take advantage of our real-time technical support to answer your questions.

Your Results. Your Interpretation. All backed by our experiences as the leader in microarray testing.

Technical Features

- Simple and user friendly; all analyses integrated in one program
- Web interface that is easily accessible from any computer, anywhere
- Secure website with 128-bit encryption
- Precise clone-to-spot imaging capabilities
- Enhanced image quality
- Results generated in printable PDF format
- Order FISH probes for validation directly from interface
- All clones are mapped and validated to ensure accurate test results
- Excellent fluorescence intensity
- Highly specific signal
- Low background noise

402 → USERNAME

404 → PASSWORD

LOGIN

Questions?

Call Service Provider 124 at 888.888.8888 to find out how your laboratory can benefit from this service, or read frequently asked questions here.

System Requirements

- Internet connection
- Internet Explorer® 6.0 or above, or Firefox® 1.0 or above
- Adobe Acrobat Reader
- Appplicant requires GenePix Results data file (*.gpr) and array images in JPEG format Return to Top

Genetic Analysis Application http://www.site.com/Experiment_Details

506

| HOME PAGE |
| PATIENT LIST |
| ACCOUNT STATUS |
| SHOW MESSAGES |
| TUTORIAL |
| SIGN OFF |

| ADD PATIENT |
| FIND PATIENT |

| ANALYSIS STATUS |
| ANALYSIS HISTORY |
| VIEW EXPERIMENTS |
| ADD EXPERIMENT SET |
| ANALYSIS REVIEW |
| ANALYSIS SUMMARY |
| PDF PLOTS |

Experiment Details — 1302

| Patient ID | less 15 |
|---|---|
| Slide # | 57359 |
| Gal File | SigChipWG_ID_23_07.gal |
| Scanner | GenePix 400B (118236) |
| Wavelengths | (635/532) |
| PMT Gain | (587,900) |
| Total Spots | 18652 |
| PCT of Spots Accepted | 99.48% |
| Total Accepted Clones | 4663 |
| PCT of Clones Accepted | 100.00% |
| PCT of Single Clones | 0.00% |
| Series | Control 647/ Patient 555 |
| GPR File | 03_CF_647_07-009438_555_057359.gpr |
| JPG File | 03_CF_647_07-009438_555_057359.jpg |
| Submitted | 6/12/2008 8:48 |

Clones with Filtered Spots — 1304

- 4648 : Xq28 RP11-665O24 : MSF
- 4634 : Xq28 RP11-1140H7 : MSF
- 4628 : Xq27.3 CTD-2501K6 : MSPF
- 4592 : Xq25 RP11-229G9 : MSF
- 4564 : Xq22.2 RP11-34P3 : MSF
- 4538 : Xq21.2 RP11-203K1 : MSF
- 4523 : Xq13.1 CTD-3090M11 : MSPF
- 4472 : Xp11.4 RP11-244N4 : MSPF
- 4462 : Xp21.1 RP11-939O17 : F
- 4353 : Xp22.33/YP11.31 RP11-953C8 : F
- 4351 : Xp22.33/YP11.31 RP11-751f9 : F
- 4279 : 22Xq11.22 RP11-891f22 : MSF

WEB-BASED GENETICS ANALYSIS

RELATED APPLICATIONS

This U.S. patent application claims the benefit of priority from and hereby incorporates by reference the entire disclosure of U.S. Provisional Application for Letters Patent Ser. No. 60/038,623, filed Mar. 21, 2008.

BACKGROUND

Chromosomes are organized structures of DNA and protein and are present in nearly every cell in our body. Each chromosome contains hundreds of genes that determine many of our exhibited personal traits, such as eye color, hair color and the like. Typically, humans have two sets of twenty-three chromosomes, one set of which is acquired from our mother and the other of which is acquired from our father.

While humans ordinarily have two copies of each autosomal region, this may vary for particular genetic regions due to DNA copy loss or gain. Many times, such loss or gain is normal and does not adversely affect the person. Unfortunately, other times such loss or gain is associated with a genetic syndrome or disorder. For instance, Down syndrome (or Trisomy 21) is a genetic disorder that is caused by the presence of some or all of an extra twenty-first chromosome. Other genetic disorders that are caused by chromosomal DNA copy loss or gain include, among others, Cri du chat, Wolf-Hirschhorn syndrome, Edward's syndrome, Jacobsen syndrome and Turner syndrome.

Currently, over 100 regions of human chromosomes are known to be associated with well-described genetic syndromes that are caused by DNA copy loss or gain. Many of these imbalances are sub-microscopic, which requires the use of complex technologies to detect these imbalances in a patient's genome. One such technology, known as array-based comparative genomic hybridization ("array CGH" or "aCGH"), has proven effective at allowing doctors and clinicians to rapidly evaluate chromosomal segment losses and gains.

To perform array CGH, a doctor or clinician extracts DNA from a patient sample. This DNA is then tagged with a fluorescent dye. A control sample from another person, meanwhile, is also prepared and tagged with a fluorescent dye of a different color. This control sample is typically taken from a person who does not exhibit any traits of a genetic disorder or syndrome. That is, the control sample should typically comprise a representation of a "normal" genome. At this point, the patient DNA and the control DNA are mixed together on a microscope slide (known as a "microarray slide") that may have, for instance, thousands of regions of chromosomes represented as dots on the slide. Each of these dots contains unique fragments of DNA from a particular section of each chromosome.

Once the patient and control DNA are applied to the microarray slide, fragments of the patient and control DNA compete to attach (or "hybridize") to the DNA fragments in each dot of the microarray slide. For each location on the slide, if the patient DNA does not have a gain or a loss, then the patient DNA should compete equally with the control DNA (assuming that the control DNA also does not have a gain or a loss at that location). If, however, the patient DNA has a loss at that location, then the control DNA will hybridize to the DNA fragment to a greater degree than will the patient DNA. Conversely, if the patient DNA has a gain, then the patient DNA will hybridize to the DNA fragment to a greater degree than will the control DNA.

After hybridization occurs, the microarray slide may be placed in a scanner that measures the fluorescent signals of each microarray dot. In instances where the patient and the control compete equally, the distinct fluorescent colors will result in the appearance of a color that reflects equal dosage of the two colors. In instances where a patient has a loss, however, the scan will result in the predominance of the fluorescent color with which the control DNA was tagged. Conversely, where the patient DNA has a gain, the scan will result in the predominance of the fluorescent color with which the patient DNA was tagged. With this information, a doctor or a clinician may determine where the patient has chromosomal segments gains and/or losses. Furthermore, with this knowledge, the doctor or clinician may formulate or verify a diagnosis for the patient. For instance, the doctor or clinician may use this information to verify (to a higher degree of certainty) that a particular patient does indeed have Down syndrome.

While array CGH and other technologies have drastically improved clinician's ability to detect DNA copy gains and losses, a need exists to leverage previously-accumulated knowledge and experience.

SUMMARY

This document describes techniques for allowing doctors and clinicians to upload genetic data associated with patients for comparison with previously-uploaded genetic data associated with other patients. These techniques may also allow doctors and clinicians to create notations associated with uploaded patient data. Both the previously-uploaded data as well as the created notations may further be used to assist doctors and clinicians in attempting to diagnose patients.

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter. The term "techniques," for instance, may refer to system(s), method(s) and/or computer-readable instructions as permitted by the context above and throughout the document.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical items.

FIG. 4 illustrates an example page served by the site of FIG. 1. This example page allows a user to authenticate at the site in order to use the genetic analysis application.

FIG. 7 illustrates yet another example page served by the site of FIG. 1. This example page allows the user to view patient data that the user has previously uploaded to the database. This page also allows the user to search for data about a particular patient.

FIG. 12 illustrates yet another example page served by the site of FIG. 1. This example page also includes information about an uploaded experiment.

FIG. 13 illustrates yet another example page served by the site of FIG. 1. This example page includes experiment details for an uploaded experiment.

FIG. 17 illustrates yet another example page served by the site of FIG. 1. This example page includes the visual representation of the slide from FIG. 15, with a portion of the visual representation having been highlighted by a user. In addition, this page includes an area where a user may order one or more fluorescent in situ hybridization (FISH) probes for the clones in the highlighted or marked region.

DETAILED DESCRIPTION

This disclosure is directed to techniques for allowing doctors and clinicians to upload genetic data associated with patients for comparison with previously-uploaded genetic data associated with other patients. These techniques may also allow doctors and clinicians to create notations associated with uploaded patient data. Both the previously-uploaded data as well as the created notations may be used by doctors and clinicians in attempting to diagnosis patients.

The described techniques may be implemented in a number of ways and in a number of contexts. One example implementation and context is provided with reference to the following figures, as described below in more detail. It is to be appreciated, however, that the following implementation and context is but one of many.

Illustrative Environment and System Architecture

Figure 1:
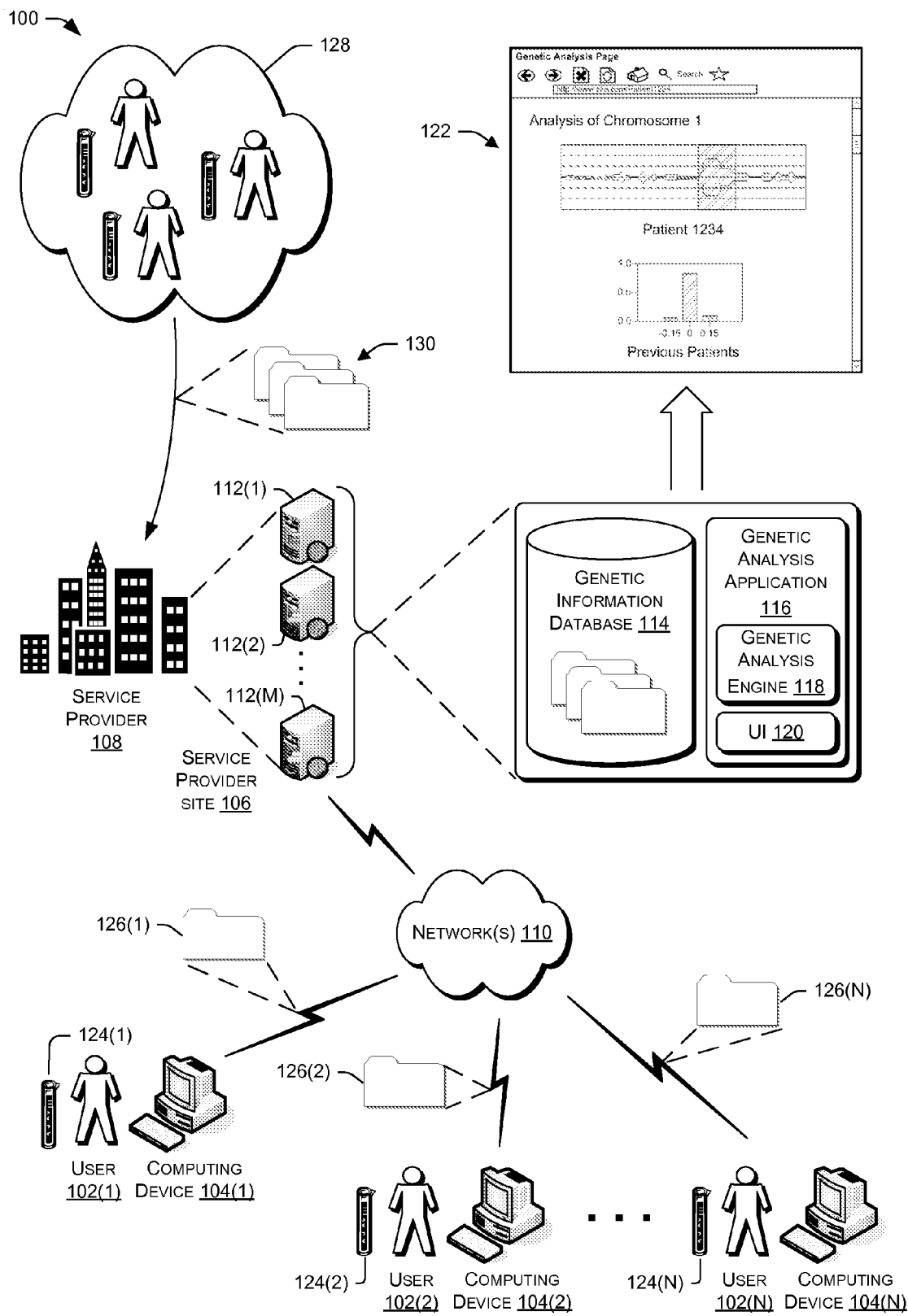
FIG. 1 illustrates an example architecture that includes a site to host a genetic analysis application that is accessible by multiple users via a network. As illustrated, these users, which may include doctors or clinicians, may upload patient data to a genetic information database for comparison of this data to other patients whose data has been uploaded previously to the database.

FIG. 1 illustrates an example architecture 100 in which the described techniques for leveraging previously-accumulated knowledge and experience for diagnosing chromosomal syndromes may be implemented. Here, the techniques are described in the context of a site hosted by a service provider. It is to be appreciated, however, that the described techniques may be implemented in a vast number of other contexts and environments.

In architecture 100, one or more representative users 102(1), 102(2), . . . , 102(N) employ user computing devices 104(1), 104(2), . . . , 104(N) to access a representative service provider site 106 associated with a service provider 108. Users 102(1)-(N) may include doctors, clinicians, health care professionals, researchers, patients, or any other person interested in providing and/or analyzing genetic data. Service provider 108, meanwhile, may be a business or other entity that hosts or otherwise operates site 106 for the purpose of allowing users 102(1)-(N) the ability to upload and research genetic data. Site 106 may comprise any sort of site that supports user interaction, such as a website accessible over the Internet. Site 106 may also comprise a proprietary site that receives requests and provides content over proprietary networks other than the Internet and public web. Furthermore, in some instances, service provider 108 may not operate a site, but may somehow otherwise make available the described application(s) and database(s) to users 102(1)-(N) over a network.

As illustrated, a user (such as user 102(1)) accesses site 106 of service provider 108 via a network 110. Network 110 may include any one or combination of multiple different types of networks, such as cable networks, the Internet, and wireless networks. User computing device 104, meanwhile, may be implemented as any number of computing devices, including as a remote terminal accessing a server, a personal computer, a laptop computer, a portable digital assistant (PDA), a cell phone, a set-top box, a game console, a personal media player (PMP), and so forth. User computing device 104 is typically equipped with one or more processors and memory to store applications and data. An application, such as browser or other client application, running on device 104 facilitates access to site 106 over network 110.

Site 106, meanwhile, is hosted on one or more servers 112(1), 112(2), . . . , 112(M) having processing and storage capabilities. In one implementation, the servers might be arranged in a cluster or as a server farm, although other server architectures may also be used to host the site. The site is capable of handling requests from many users and serving, in response, various pages of content that can be rendered at user computing devices 104(1)-(N) for viewing by user 102(1)-(N). It is noted that while the proceeding discussion describes the techniques with reference to pages, it is to be appreciated that the described techniques are equally applicable to other types of user interfaces (UIs). That is, the described techniques may apply to any sort of interface that includes visual content.

As illustrated, servers 112(1)-(M) host a genetic information database 114, as well as a genetic analysis application 116. Genetic information database 114 stores data about multiple patients. As discussed in detail below, this stored data may be uploaded by a plurality of users at a plurality of locations (e.g., users 102(1)-(N)), as well as by service provider 108. As such, genetic information database 114 stores a multitude of patient data for use in leveraging previously-acquired knowledge and experience associated with the stored data.

Genetic analysis application 116, meanwhile, may comprise a web-based application that includes a genetic analysis engine 118 and a user interface (UI) component 120. Genetic analysis engine 118 may analyze the patient data stored in genetic information database 114 for use in calculating statistics regarding this data. For instance, engine 118 may determine, for each autosomal region, how often patients associated with this data have exhibited chromosomal gain or loss. Engine 118 may also store notations about particular pieces of stored genetic data, which again may be provided by users 102(1)-(N) and/or by service provider 108.

User interface component 120, meanwhile, functions to output the information provided by analysis engine 118 for rendering on user computing devices 104(1)-(N). Furthermore, UI component 120 may also output for rendering information about a particular patient's data. This information may include, for instance, a visual representation (e.g., a plot) of some or all of the genome for a particular patient, uploaded by one of users 102(1)-(N) or by service provider 108. With this information, site 106 may serve pages, such as illustrated page 122, to user computing devices 104(1)-(N).

As illustrated, page 122 includes both a visual representation of chromosomal DNA copy number gain or loss for chromosome 1 of a particular patient, as well as statistics about previously-uploaded patient data, as calculated by genetic analysis engine 118. For instance and as illustrated, page 122 may include the plot of the particular patient's data, as well as statistics depicting how often chromosomal copy loss or gain have been found in the previously-uploaded patient data. Of course, while FIG. 1 illustrates an illustrative page 122, site 106 may serve multiple other pages, as illustrated and described below and otherwise.

With this architecture in mind, FIG. 1 further illustrates that users 102(1)-(N) may analyze a respective patient sample 124(1), 124(2), . . . , 124(N) to determine corresponding patient data 126(1), 126(2), . . . , (N). For instance, users 102(1)-(N) may each utilize a particular laboratory (in fact, each may utilize a different laboratory) to perform array CGH or CGH testing on patient samples 124(1)-(N). Additionally or alternatively, users 102(1)-(N) may employ a different form of genetic testing that does not involve CGH. In either instance, this testing may somehow describe or illustrate chromosomal segment loss and/or gain, information about single nucleotide polymorphisms (SNPs), sequence information generally, or any other type of genetic data including regions of loss of heterozygosity (LOH) for some or all of a corresponding patient's genome. Users 102(1)-(N) may then upload patient data 126(1)-(N) to genetic information database 114 via computing devices 104(1)-(N). Furthermore, in some instances, users 102(1)-(N) may upload genetic data without having performed any sort of tests. In these instances, this data may have been previously compiled by another entity.

Once this data has been uploaded, each of users 102(1)-(N) may then operate, at a corresponding computing device 104(1)-(N), genetic analysis application 116. For instance, these users may use application 116 to compare their uploaded data against previously-uploaded data in hopes of better diagnosing a subject/patient.

To illustrate, user 102(1) may upload patient data 126(1) in order to compare this data against previously-uploaded data associated with multiple other patients. User 102(1), who may be a doctor or a clinician, may then determine that while his or her patient does indeed show a chromosomal DNA copy loss or gain at a particular location, the previously-uploaded information shows that such a loss or gain is commonly found without adverse affects among many people. Conversely, user 102(1) may learn, via application 116, that his or her patient's DNA copy loss or gain occurs at a location that is commonly associated with a particular genetic syndrome. In either instance, user 102(1) is able to leverage previously-accumulated knowledge and is able to better serve his or her patient.

While each of users 102(1)-(N) may perform the genetic testing (e.g., array CGH) of patient samples 124(1)-(N), in some embodiments these users may also choose to have service provider 108 directly perform this testing. For instance, user 102(1) may physically send patient sample 124(1) to service provider 108. One or more representatives 128 (e.g., doctors, clinicians, etc.) of service provider 108 may then perform the testing of sample 124(1) to create patient data 126(1).

Service provider 108 may then either provide this data to user 102(1), who may then upload the data to site 106 and database 114, or service provider 108 may directly upload data 126(1) to database 114. User 102(1) may then navigate to site 106 to analyze data 126(1) along with the previously-uploaded patient data. As illustrated, FIG. 1 depicts that representatives 128 of service provider 108 test patient samples to create a set of patient data 130 for uploading to the genetic information database 114.

Figure 2:
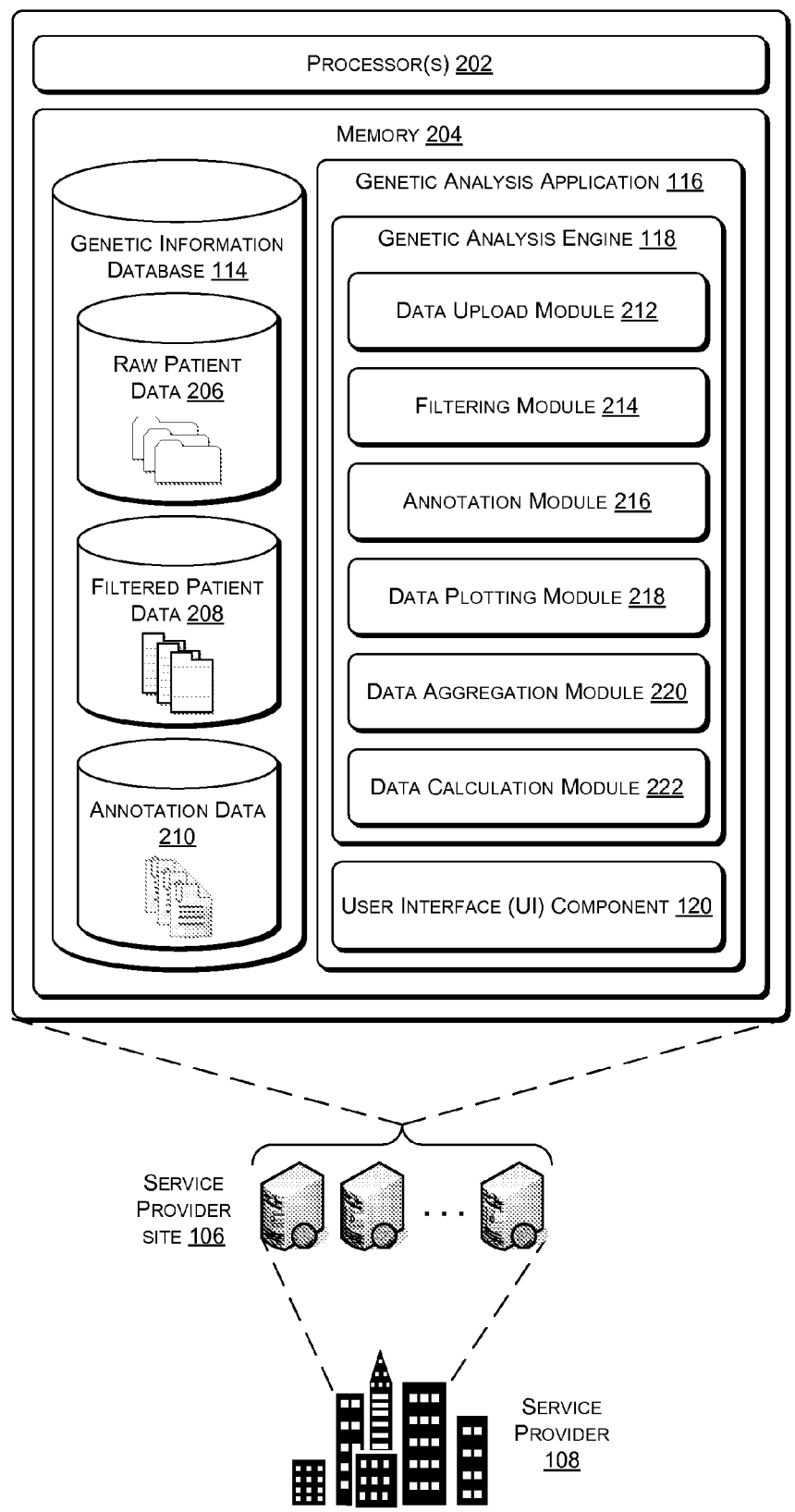
FIG. 2 illustrates example components of the genetic analysis application and the genetic information database of FIG. 1.

FIG. 2 depicts illustrative components of the genetic information database and the genetic analysis application described above. As illustrated, servers 112(1)-(M) of site 106 include processors 202 and memory 204, which stores database 114 and application 116.

In some implementations, genetic information database 114 includes raw patient data 206, filtered patient data 208 and notation data 210. While all of this data may be stored in database 114 in some instances, in other instances each of these types of data may be stored in a separate and distinct database. Raw patient data 206 comprises data that has been uploaded by users (e.g., users 102(1)-(N) and representatives 128) before site 106 has processed the data. Filtered patient data 208, meanwhile, may comprise patient data that site 106 has processed. For instance, while raw patient data 206 may include all or substantially all of the information learned during the genetic testing (such as array CGH), filtered patient data 208 may include only the information regarding chromosomal DNA copy loss or gain. Finally, notation data 210 may include notations made by users (e.g., users 102(1)-(N) and representatives 128) or by some external entity, such as a remote database that provides information regarding genetic syndromes.

Next, genetic analysis application 116 includes genetic analysis engine 118 and UI component 120. Genetic analysis engine 118, meanwhile, may include a data upload module 212, a filtering module 214, a notation module 216, a data plotting module 218, a data aggregating module 220, and a data comparator module 222.

Data upload module 212 functions to allow users (e.g., users 102(1)-(N) and representatives 128) to upload raw patient data (e.g., patient data 126(1)-(N) and patient data 130) to genetic information database 114. Specifically, module 212 allows these users to upload this data to a database or a location in database 114 that stores raw patient data 206. Filtering module 214 then functions to filter this uploaded raw patient data 206. For instance, module 214 may filter out information that does not identify a chromosomal DNA copy loss or gain. As such, module 214 may create filtered patient data 208 that generally only includes those regions that may contain a chromosomal abnormality. Of course, in some instances, engine 118 may not filter this data, in which case database 114 may store raw patient data 206 but not filtered patient data 208.

In some instances, patient samples 124(1)-(N) are placed onto array CGH or CGH slides in the form of bacterial artificial chromosome (BAC) arrays. In other instances, patient samples 124(1)-(N) are placed onto array CGH or CGH slides in the form of oligonucleotide (oligo) arrays. While both BAC and oligo arrays tend to be successful in enabling identification of losses and gains, oligo arrays tend to enable even better identification due to the fact that they comprise smaller regions of a chromosome. Furthermore, because oligo arrays comprise smaller regions of a chromosome than compared to BAC arrays, oligo arrays tend to include many more spots than BAC arrays. For instance, a slide comprising an oligo array may include approximately 105,000 spots, while BAC array slide may include approximately 4,700 spots. Because of the large number of spots that comprise an oligo array, patient data garnered from these arrays tend to be much larger than data garnered from BAC arrays.

Therefore, in some instances filtering module 214 may filter out patient data that is based on oligo arrays, but not patient data that is based on BAC arrays. Specifically, genetic information database 114 may store all or substantially all of the information uploaded for a BAC array, while only storing the regions of potential DNA copy losses or gains as filtered by module 214 for oligo arrays.

In addition to data upload module 212 and filtering module 214, genetic analysis engine 218 includes data plotting module 216. Data plotting module 216 functions to receive patient data (e.g., stored as raw patient data 206 or filtered patient data 208) and create a plot for the data. This plot may indicate, for instance, a degree of chromosomal segment loss or gain for some or all of the uploaded chromosome information. Furthermore, module 218 may create a plot for the entirety of the corresponding patient data, as well as plots for smaller pieces of this data. For instance, module 218 may create plots for each chromosome associated with the uploaded data.

Next, data aggregation module 220 functions to aggregate previously-uploaded patient data based on requests made by a user of application 116. For instance, if a user (e.g., user 102(1)) wishes to view his or her patient data at chromosome 1, data aggregation module 220 may aggregate information about chromosome 1 based on the previously-uploaded patient data. Data calculation module 222 may then calculate statistics regarding this aggregated data. For instance, module 222 may determine (and output for the user) statistics indicating how often chromosomal DNA copy losses and/or gains have been found in the aggregated data for chromosome 1 or for some portion of chromosome 1.

If, for instance, user 102(1) wishes to focus on a particular portion of chromosome 1 associated with his or her patient (e.g., a portion that appears, according to the plot, to have a DNA copy gain or loss), then data aggregation module 220 may aggregate corresponding data and data calculation module 222 may calculate statistics about gain or loss previously seen at this location. Of course, while one specific type of statistics has been discussed, data calculation module 222 may similarly calculate any other type of statistics regarding the previously-uploaded data.

Finally and as discussed above, UI component 120 functions, at least in part, to receive the created plots, notations and calculated statistics for creation of one or more user interfaces. User interface component 120 may output this and other data for the rendering of page 122 illustrated in FIG. 1, as well as for multiple other pages and UIs including those discussed below.

Figure 3:
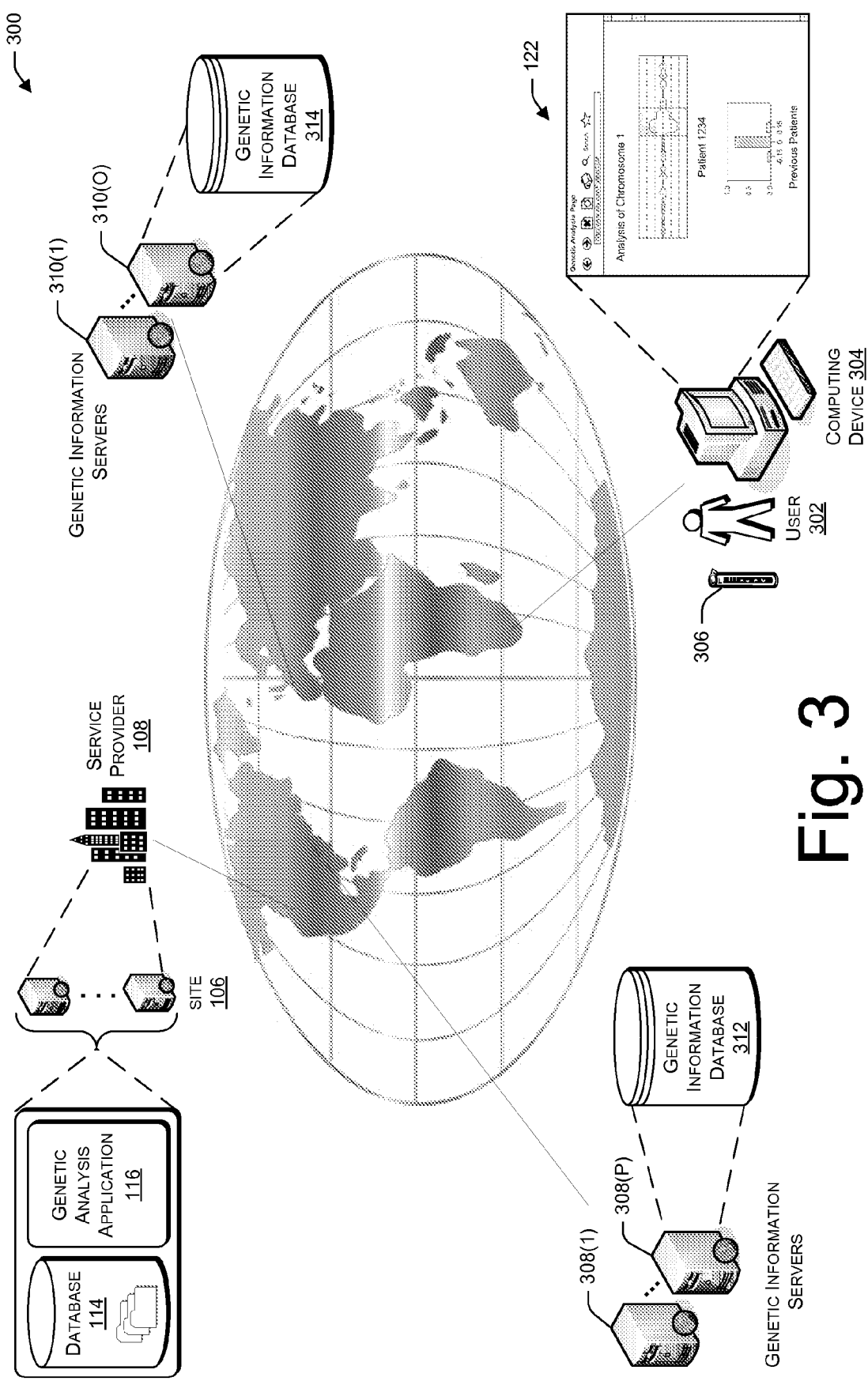
FIG. 3 illustrates that, in some embodiments, users spread out in multiple locations around the globe may access the genetic analysis application and the genetic information database of FIG. 1.

FIG. 3 illustrates an environment 300 in which service provider 108 and site 106 may host genetic information database 114 and genetic analysis application 116. Specifically, environment 300 represents that, in some instances, users may access genetic analysis application 116 from anywhere in the world. Furthermore, environment 300 illustrates that database 114 (and, hence, application 116) may leverage information from all over the world by pulling this information from remote sources.

In the illustrated implementation, a user 302 (e.g., a doctor, clinician, or other health care professional) operates a computing device 304 to operate genetic analysis application 116, possibly to analyze data associated with his or her patient sample 306. As such, application 116 may serve and device 104 may render a page such as page 122 illustrated by and described with reference to FIG. 1. In the instant example, user 302 is shown accessing application 116, which is hosted by site 106 in the northern United States, from the other side of the equator in South Africa. Similarly, in the illustrated environment, users may access site 106 via a network from all around the globe.

Furthermore, environment 300 includes a first set of genetic information servers 308(1), . . . , 308(P), as well as a second set of genetic information servers 310(1), . . . , 310(O). Each of these sets of servers (operating in the Eastern United States and Europe, respectively) may include or have access to a genetic information database, such as genetic information databases 312 and 314, respectively. Genetic information databases may include a sequenced listing of the human genome, a genome browser, patient data, information correlating particular DNA copy loss or gain with particular genetic syndromes, or any other type of genetic information. In each of these instances, site 106 may pull information from databases 312 and 314 for supplementing information stored in database 114. As such, environment 300 represents that genetic analysis application 116 may leverage genetic information from all around the globe in addition to patient data uploaded to database 114 by doctors, clinicians and the like. This global information may further help these doctors and clinicians in diagnosing patients, or otherwise making determinations regarding associated patient data.

Illustrative User Interfaces

FIG. 4 depicts an example "sign-on" page 400 served by site 106 of FIG. 1. This sign-on page allows a user to authenticate at the site for the purpose of using genetic analysis application 116. In addition to information about the application, such as technical features, system requirements, and the like, page 400 here includes a text box 402 for providing a valid username and a text box 404 for providing a corresponding password. While page 400 here allows a user to sign on with a username/password combination, other implementations may authenticate users in many other ways (e.g., biometric information, one-time passwords, etc.).

Figure 5:
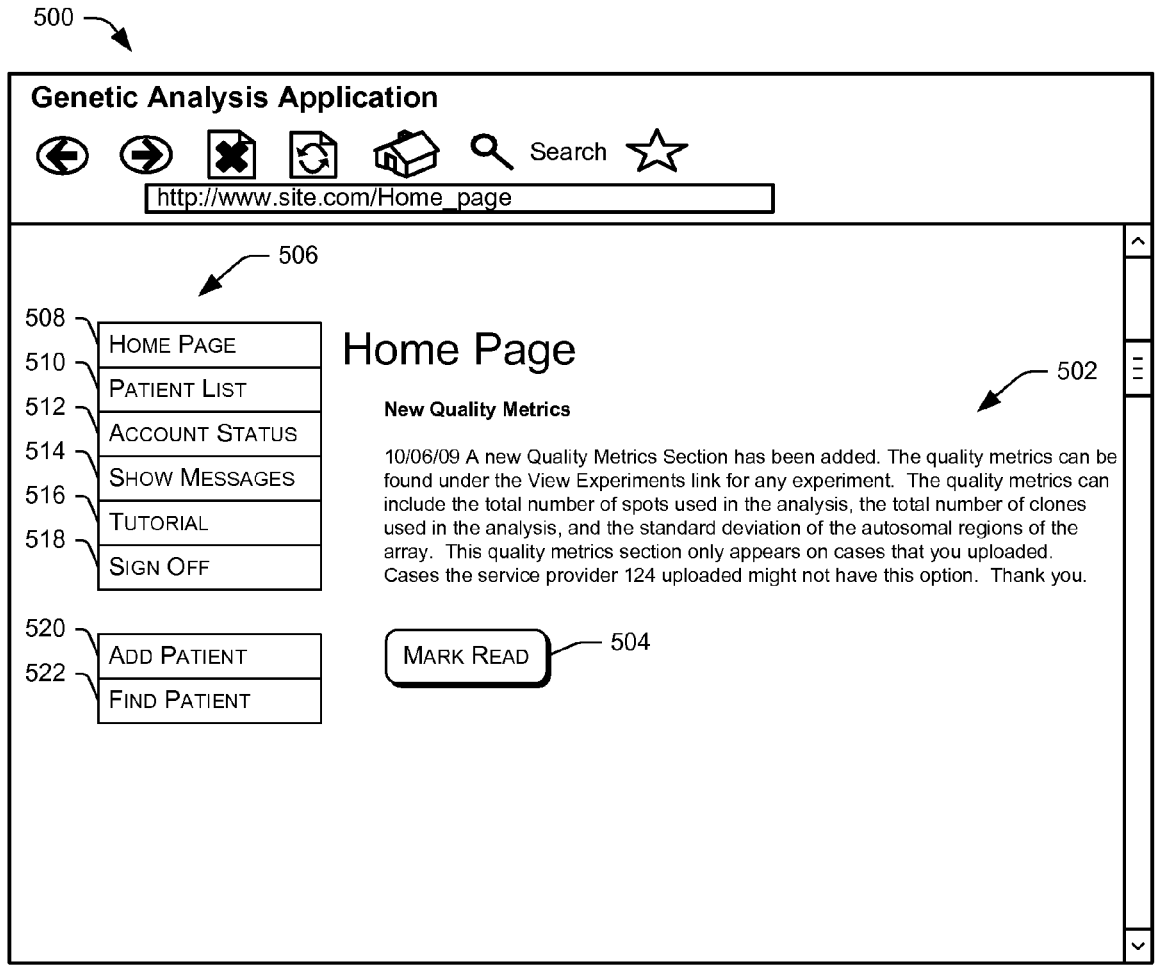
FIG. 5 illustrates another example page served by the site of FIG. 1. This example page comprises a home page that the site serves to the user after authenticating at FIG. 4.

FIG. 5 illustrates an example home page 500 served by the site of FIG. 1 after the user has authenticated or signed on via page 400 of FIG. 4. Home page 500 may include recent and potentially important message(s) 502 about application 116, as well as an icon 504 that, when selected, allows the user to mark a messages as already read. Home page 500 may also include a menu of links 506, each of which results in navigation to a corresponding page when selected. Menu 506 includes links entitled home page 508, patient list 510, account status 512, show messages 514, tutorial 516, sign off 518, add patient 520 and find patient 522. Many of the pages associated with these links are illustrated and described below in detail.

Figure 6:
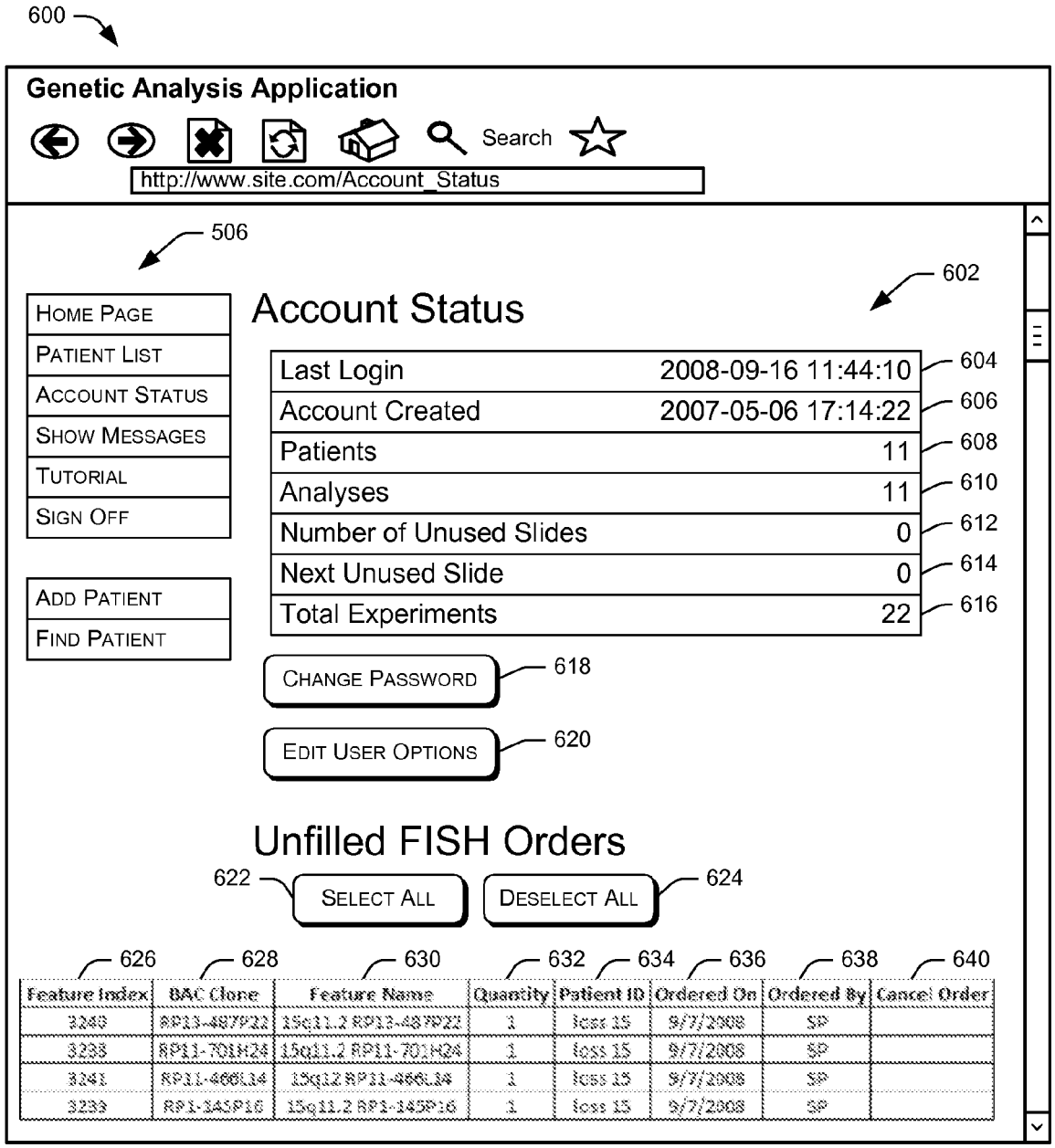
FIG. 6 illustrates yet another example page served by the site of FIG. 1. This example page comprises an account status for the account associated with the authenticated user.

FIG. 6, for instance, illustrates an example account status page 600 that site 106 serves after a user selects icon 512 from menu 506. This page, entitled "Account Status," includes information 602 such as a last time the user logged in 602, when the account was created 606, a number of patients 608 that the user has provided data for, a number of analyses 610 run by the user on this patient data, a number of unused slides 612, the next unused slide 614 (if applicable), and the total number of experiments 616 that the user has conducted. Account status page 600 may also include an icon 618 that, when selected, allows the user to change his password. Page 600 also illustrates an icon 620 to allow the user edit user options.

Account status page 600 may also include an area that lists those fluorescent in situ hybridization (FISH) probes that the user has ordered, as well as the status of those orders that allows the user to track, modify and/or cancel one or more orders as the user desires. For instances, in the illustrated embodiment, page 600 illustrates that some of the user's orders remain unfilled. In some instances, the user may order FISH probes as a back-up test to determine whether or not a patient does indeed have a deletion, duplication, translocation, or some other complex rearrangement at particular locations. For instance, if a user employing genetic analysis application 116 believes that a patient has a DNA copy loss at a particular portion of an uploaded BAC array, the user may choose to order a FISH probe at this location of the BAC array. The user may then use this received FISH probe as a check on the user's hypothesis regarding the patient's gain or loss. Here, page 600 represents that the user has ordered several FISH probes whose orders have yet to be filled.

Page 600 includes icon 622 that, when selected, selects all of the unfilled FISH probes, as well as an icon 624 that, when selected, de-selects all of the unfilled FISH probes. The listing of the unfilled FISH probes includes indications, for each clone, of: a feature index 626 of the clone, the corresponding BAC clone 628, the feature name 630, the quantity ordered 632, the patient ID 634, the date 636 on which the user ordered the probe, an indication 638 of who ordered the probe (here, service provider 108), as well as an area 640 where the user can select to cancel the order.

Figure 7:
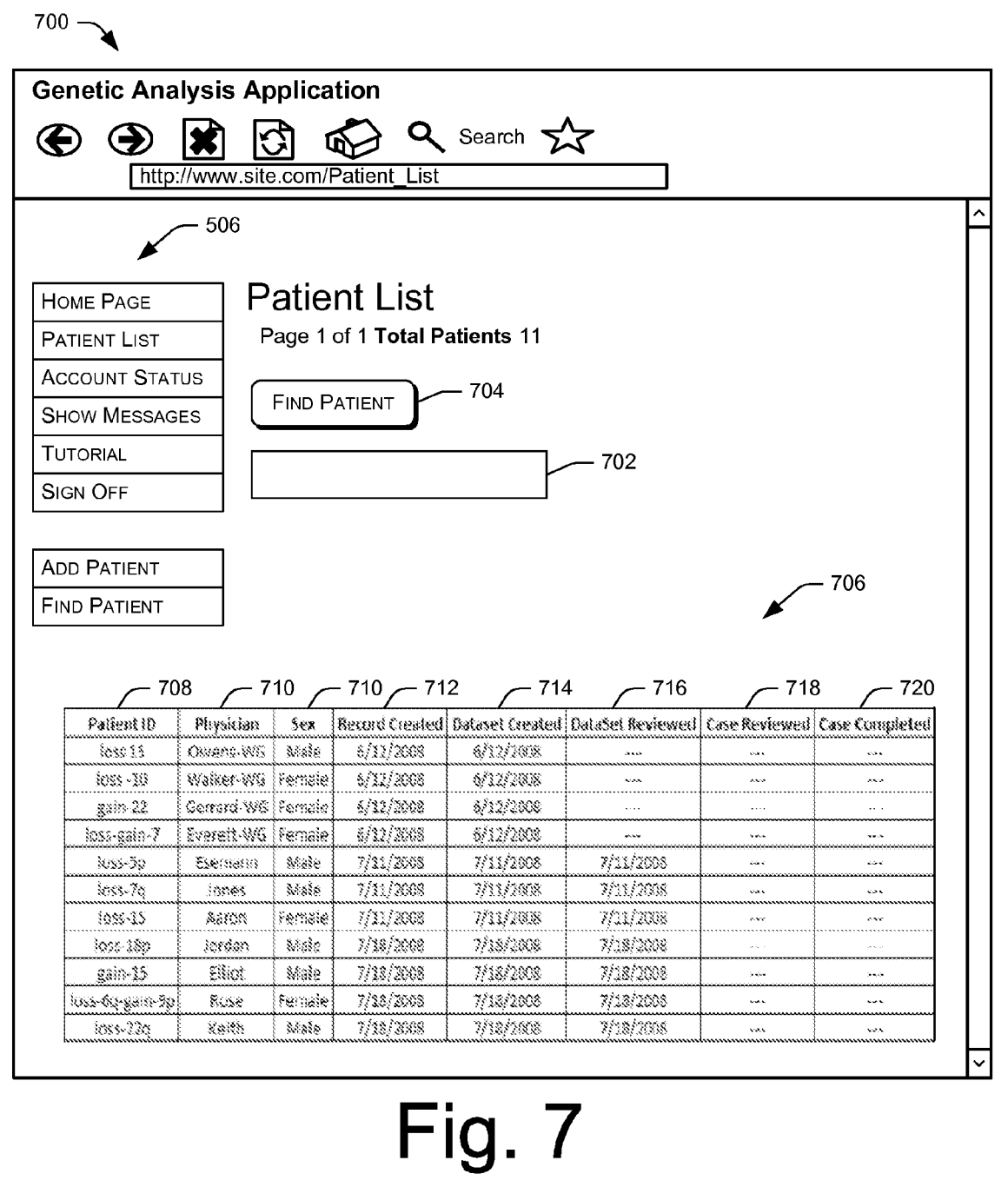

FIG. 7 illustrates an example patient list page 700 served by the site of FIG. 1. This example page allows the user to view patient data that the user has previously uploaded to the database, as well as search for data about a particular patient. As illustrated, page 700 includes a text box 702, in which a user may enter a desired patient's identification, and an icon 704. Selection of icon 704 initiates a search based on the identification or other information entered in text box 702. After the search is initiated, site 106 may serve a new page that includes any received search results.

Page 700 also includes a list 706 of patients. List 706 may comprise those patients that the currently signed-in user has uploaded to site 106. List 706 includes, for each patient, an indication of: an identifier 708 of the patient, a physician 710 that is associated with the patient (e.g., that uploaded or analyzed the patient's data), a date 712 on which the patient's record was created, a data 714 on which the patient's dataset was created (e.g., uploaded to the site), a date 716 on which this dataset was reviewed (e.g., by the user viewing the page or by another physician, clinician, etc.), a date 718 on which the case was reviewed and a date 720 on which the case was completed.

Furthermore, the user may sort the illustrated table by each piece of information included in list 706. For instance, the user may double-click the header associated with the referring physician to sort the table (e.g., alphabetically) by the listed referring physicians. While list 706 includes a multitude of information about each listed patient, other implementations may include more or less information than the illustrated implementation.

Figure 8:
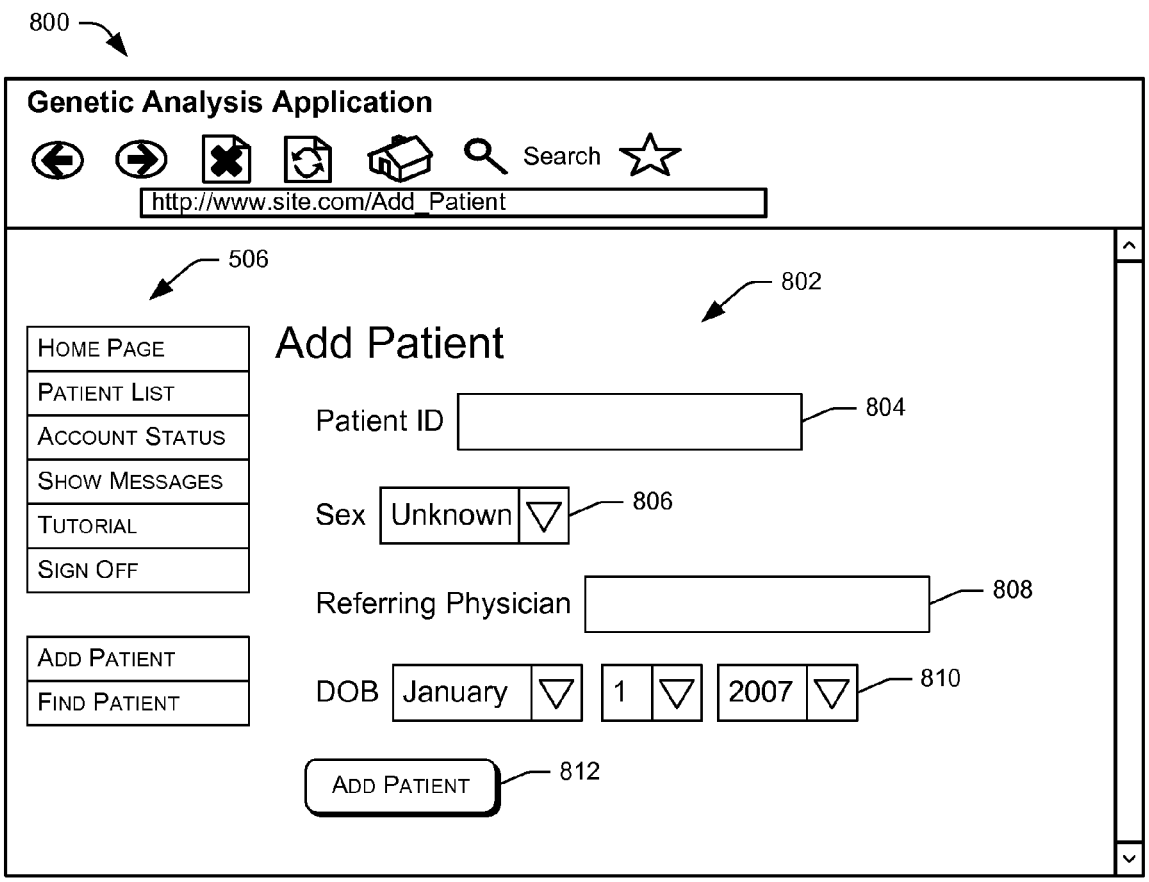
FIG. 8 illustrates yet another example page served by the site of FIG. 1. This example page allows the user to add a patient to the genetic information database.

FIG. 8 illustrates an example page 800 served by the site of FIG. 1 in response to the user selected icon 520 (entitled "Add Patient"). As this page's name suggest, page 800 includes an area 802 that allows the user to add a patient to the genetic information database. To do so, the user may first enter a patient's identifier (which may be anonymous in some instances) into text box 804. Next, the user may select a gender or sex of the patient via a drop-down menu 806. The user may also enter, into a text box 808, the name of the referring physician. Finally, the user may select the patient's date of birth (via drop-down menus 810) and select an icon 812 ("Add Patient") to add the patient to the database.

Figure 9:
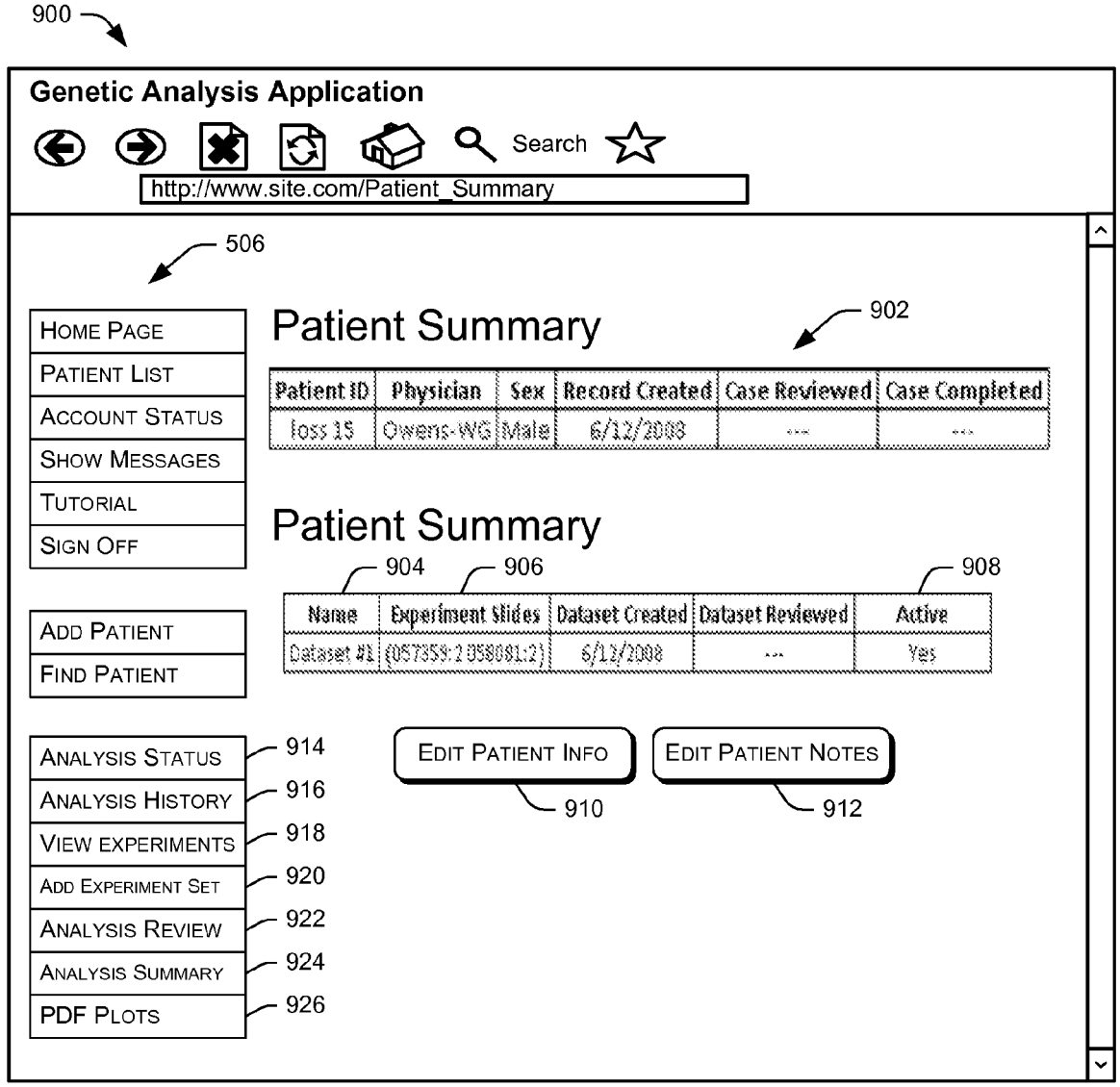
FIG. 9 illustrates yet another example page served by the site of FIG. 1. This example page displays information about one or more particular patients.

FIG. 9 illustrates an example page 900 that site 106 may serve after a user has added a patient to the site via page 800 or when the user otherwise chooses to view patient information. Page 900, entitled "Patient Summary," displays information about one or more particular patients. Here, page 900 includes information 902 about a patient identified as "loss 15" (meaning that this patient exhibits a DNA copy loss in chromosome 15). In addition to the information listed in previous pages, page 900 includes a name 904 of the first dataset associated with the patient, an indication 906 of the slides from which the data was uploaded, and an indication 908 of whether or not the case is active. Furthermore, page 900 includes icons 910 and 912 that, when respectively selected, allow the user to edit the listed patient information and edit notes associated with the patient.

Page 900 also includes additional links in menu 506, including links entitled analysis status 914, analysis history 916, view experiments 918, add experiment set 920, analysis review 922, analysis summary 924 and PDF plots 926. Each of links, when selected, causes navigation to an associated page or pages served by site 106. Many of these pages are illustrated and described below.

Figure 10:
FIG. 10 illustrates yet another example page served by the site of FIG. 1. This example page allows the user to upload array comparative genomic hybridization (CGH) data to the genetic information database.

FIG. 10 illustrates an example page 1000 served by the site of FIG. 1 after the user has selected the link 920 entitled "Add Experiment Set" from FIG. 9. Page 1000 allows the user to upload array comparative genomic hybridization (CGH) data to the genetic information database. While page 1000 relates to array CGH information, it is noted that other implementations may allow the user to upload array information, or data created by any other type of genetic testing.

As illustrated, page 1000 includes an area 1002 that indicates the patient ID ("loss 15") as well the client ("test"). This page also allows the user to select, via drop-down menus 1004 and 1006, a control type (e.g., male or female) and a reason. Furthermore, page 1000 illustrates that genetic analysis application 116 allows a user to upload information about a first array CGH experiment 1008 for the control/patient combination, as well as a second array CGH experiment 1010 for the same control/patient combination performed in a reverse manner from the first (i.e., by reversing the dies on the slide). By performing two experiments (reverse from one another), the data gleaned from the experiments is even more reliable.

First experiment 1008 includes a drop-down menu 1012 that allows the user to choose to "upload new data" for this experiment. A text box 1014 is also included, within which the user may enter an identification of a slide to upload. Furthermore, the area associated with first experiment 1008 includes a text box 1016 in which a user may choose which GenePix Results (.GPR) file to upload to site 106. To select this file, the user may browse his or her computing device via an icon 1018. Page 1000 also includes a text box 1020 in which the user may choose which slide image (.JPG) file to upload. Slide images comprise actual representations (e.g., pictures) of the slides from which the data has been compiled. Again, the user may select these files with use of a browse icon 1022.

Second experiment 1010 similarly allows the user to upload new data regarding this reversed experiment. For instance, this area includes a drop-down menu 1024 that allows the user to choose to upload new data, a text box 1026 that allows the user to identify the slide(s), a text box 1028 that allows a user to identify a .GPR file with use of a browse icon 1030, as well as a text box 1032 that allows the user to identify the slide image(s) with use of another browse icon 1034. Finally, once the user has made all of his or her selections regarding both experiments, the user may submit or upload this data via selection of an icon 1036.

Figure 11:
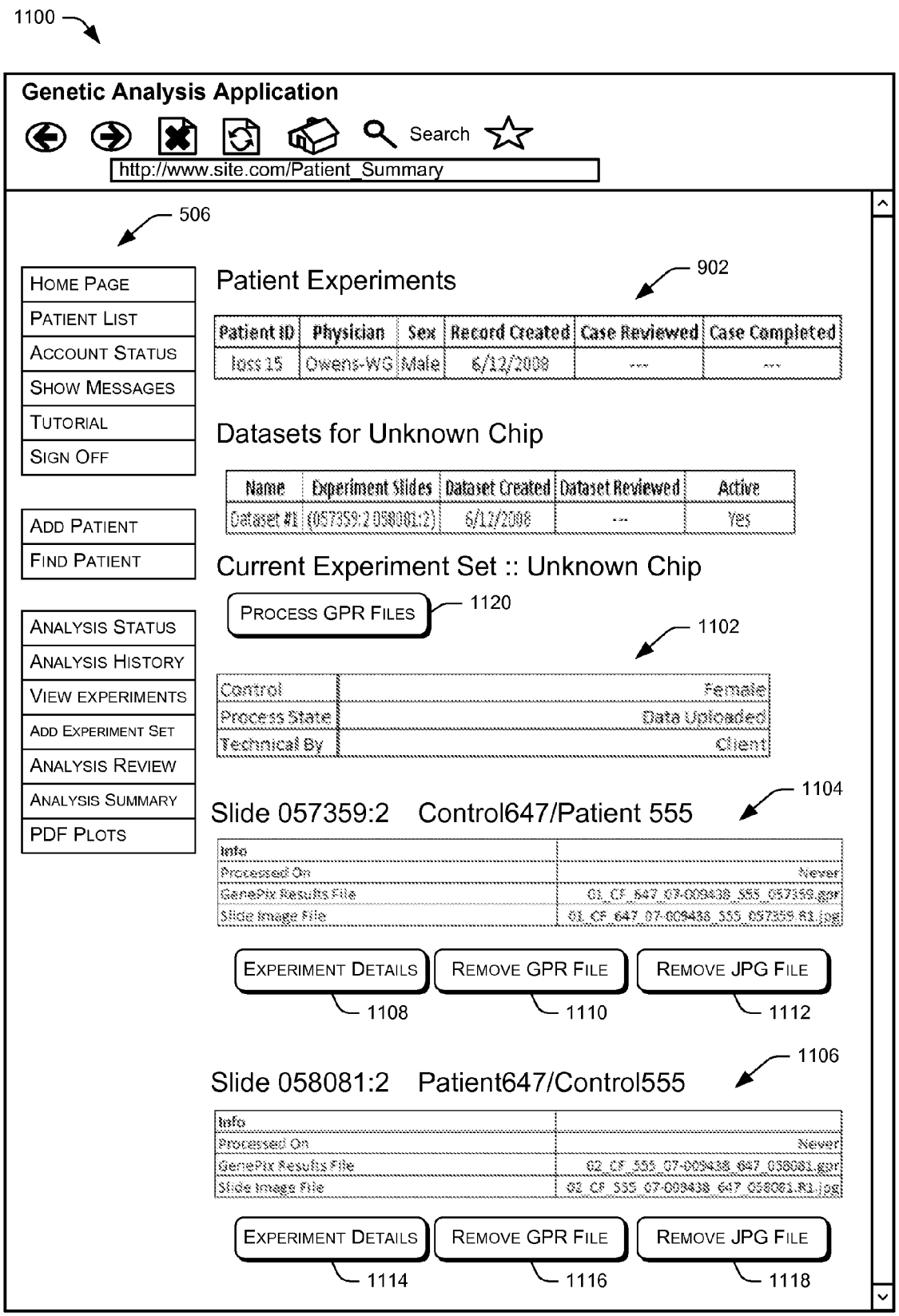
FIG. 11 illustrates yet another example page served by the site of FIG. 1. This example page includes information about an uploaded experiment.

FIG. 11 illustrates an example page 1100 that site 106 serves after the user has submitted the data from page 1000. Page 1100 allows the user to view information 1102 about the control, the process state, and who uploaded the data, as well as information 1104 about the first uploaded experiment and information 1106 about the second uploaded experiment. As such, this page allows the user to review the information about these experiments to ensure their accuracy. If the user determines that certain details about the first experiment should be changed, then the user may select an icon 1108 to do so. Furthermore, if the user determines that he or she selected an incorrect .GPR and/or .JPG file on page 1000, then the user may select icon 1110 or icon 1112, respectively, to remove these files.

Page 1100 similarly affords the user the opportunity to alter information 1106 about the second experiment. Again, the page includes an icon 1114 that allows the user to change details of the second experiment, as well as icons 1116 and 1118 that allow the user to remove .GPR files and .JPG files, respectively.

Once the user has made his or her changes, if applicable, and is satisfied with the accuracy of the information, then the user may select an icon 1120 entitled "Process GPR Files." At this point, the information will be processed and site 106 may serve a patient summary page.

Figure 12:
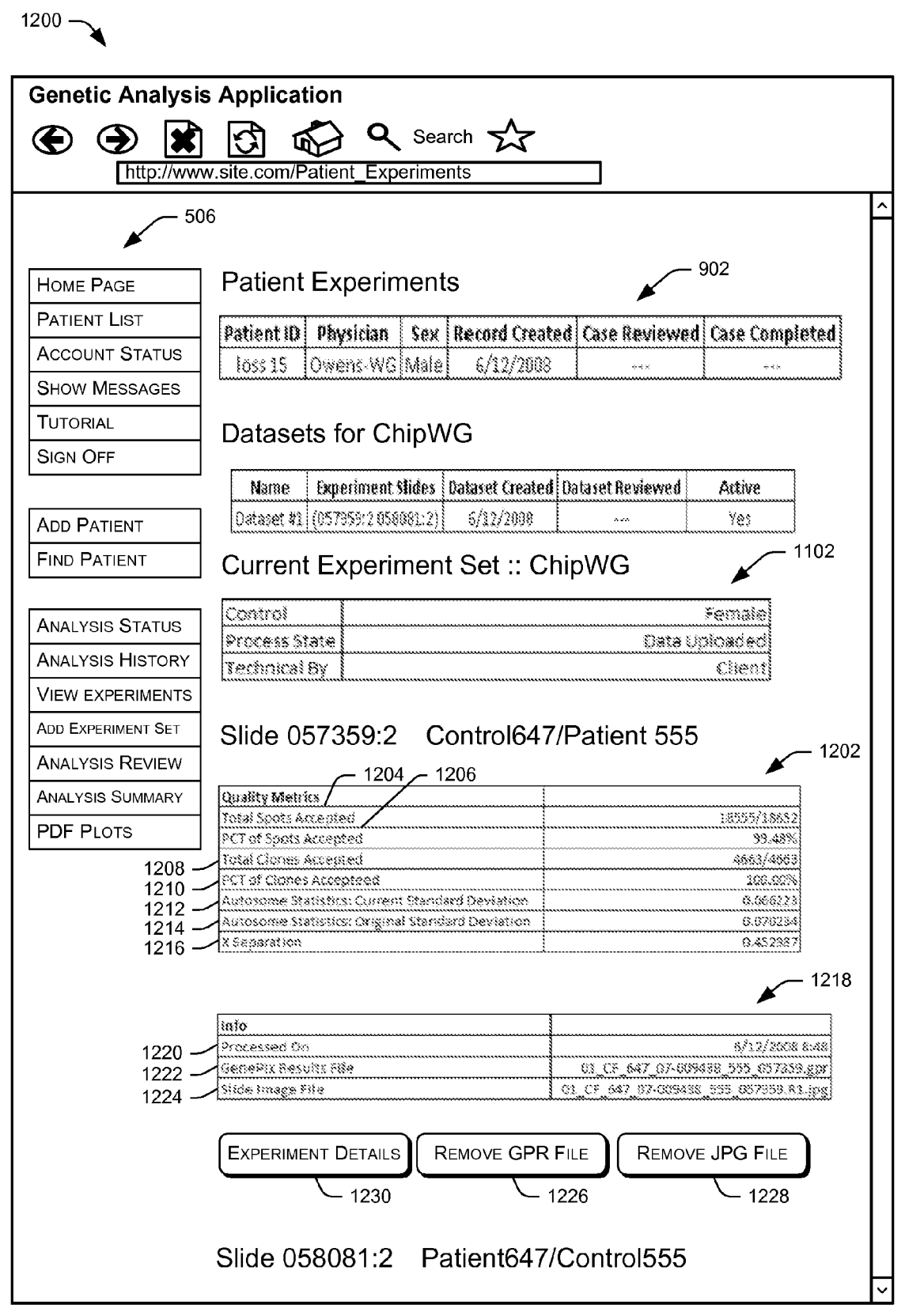

FIG. 12 illustrates an example page 1200 that site 106 may serve after the user selects link 918 ("View Experiments") from menu 506. This page will serve details about the experiment(s) marked as active. Page 1200 includes information 1102 about the control, the process state, and who uploaded the data. Page 1200 also includes information 1202 about particular slides of the first experiment from FIG. 11. This information includes a total number of spots accepted from the slides 1204, which represents a raw number of spots that were used in calculating data about the patient. The system may not have used some spots due to errors in the spot or the slide (e.g., if the slide contains a scratch or smudge, or if the spot hybridized poorly). Information 1202 also indicates a percentage of total spots accepted 1206. Here, page 1220 indicates that 99.48% of the spots were accepted.

Information 1202 further includes a total number of BAC clones accepted 1208, as well as a percentage of clones accepted 1210 (here, 100%). This page also displays a current standard deviation 1212 for the experiment, as well as an original standard deviation 1214. Finally, information 1202 includes an amount of X separation 1216.

Page 1200 may further include information 1218 about the processing of the first experiment. For instance, information 1218 here includes an indication 1220 of when the experiment was processed, an identification 1222 of the .GPR file, as well as an identification 1224 of the slide image file (.JPG). Similar to above, page 1200 also includes icons 1226 and 1228 that allow the user to remove a .GPR and .JPG file, respectively. Finally, page 1200 includes a link 1230 that, when selected, navigates to a page having even more specific details about the experiment.

FIG. 13 illustrates an example experiment details page 1300 that site 106 may serve after the user has selected link 1230 from page 1200. As illustrated, page 1300 may include experiment details 1302, some of which may have been listed in page 1200. For instance, details 1302 may include an identification of the page, a number of the slide, an indication of the .GAL file, an indication of an associated scanner, an indication of wavelengths, and an indication of PMT gain. Details 1302 may also include a total number of spots, a total number of spots accepted, a total number of accepted clones, a percentage of clones accepted, a percent of single clones, the experiment series, an identification of the .GPR and .JPG files, and a date that the data was submitted.

Page 1300 may also include a list 1304 of those clones in the experiment that include filtered spots. That is, list 1304 lists those clones that the system automatically filtered out and did not use because of a poor quality of the spot (e.g., the slide was scratched, smudged, etc.). Furthermore, each of these listed clones in list 1304 may include a link that, when selected, provides information about the associated clone that was filtered out from the experiment. For instance, this link may lead to a page that includes a reproduction (e.g., a visual picture) of the clone.

Figure 14:
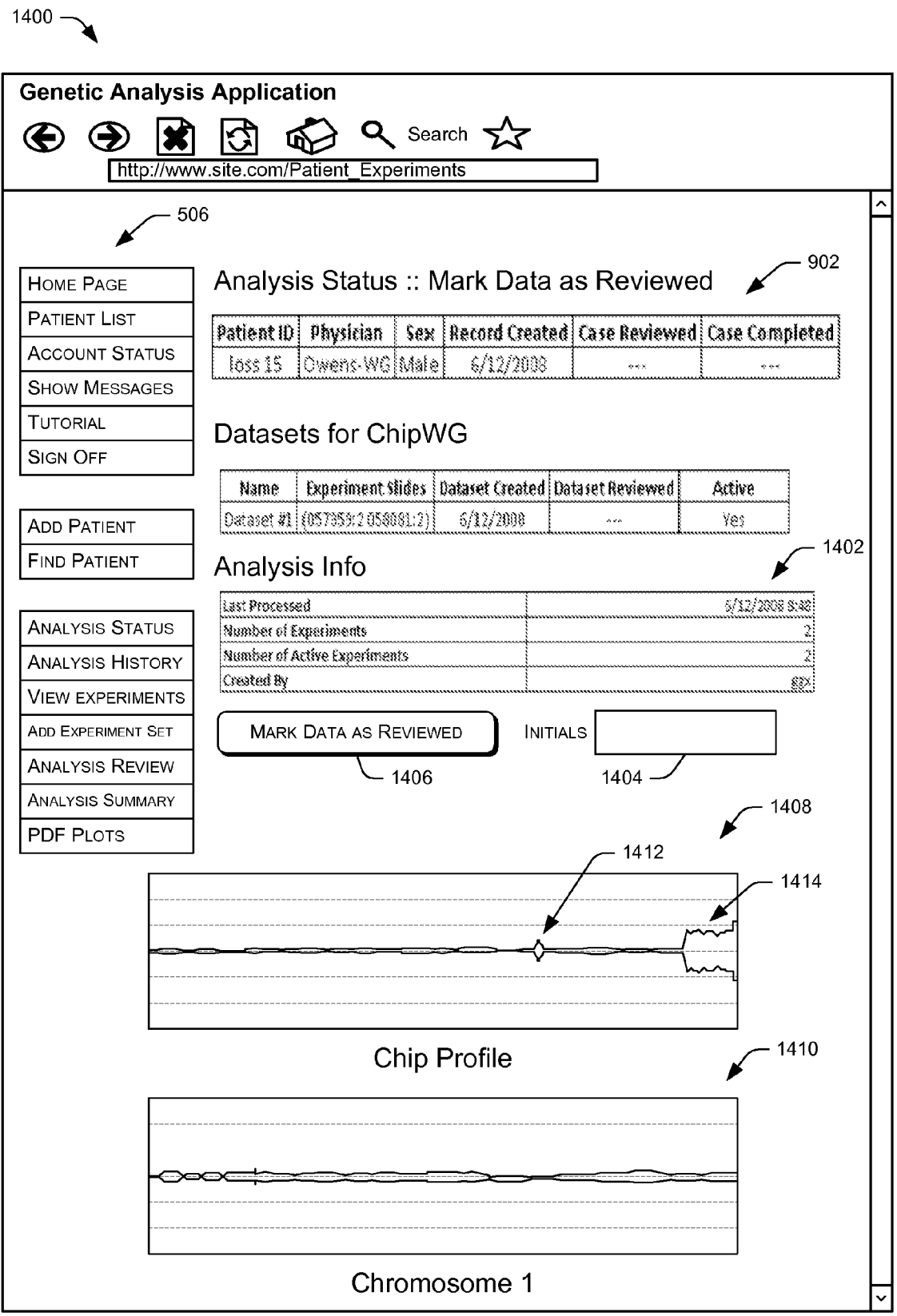
FIG. 14 illustrates yet another example page served by the site of FIG. 1. This example page includes an analysis status for an uploaded experiment. This page further includes a visual representation of the slide on which the experiment is based.

FIG. 14 illustrate an example analysis status page 1400 served by site 106 after a user selects link 914 ("Analysis Status") from menu 506. Page 1400 includes information 902 about the patient and the experiment, as well as analysis information 1402. Analysis information 1402 includes the date that the slide was last processed, the number of experiments that the user has ran, the number of active experiments, and an identification of who created the illustrated analysis (e.g., service provider 108). Once a user has reviewed this data and is satisfied with the information, he or she may choose to enter his or her initials into a text box 1404 and select to mark the data as reviewed via selection of an icon 1406.

Page 1400 also includes one or more visual representations of the uploaded patient data. For instance, page 1400 may include a plot that visually indicates whether a patient exhibits any chromosomal DNA copy loss and/or gain. Here, page 1400 includes a plot 1408 of the patient's entire uploaded genome, as well as a plot 1410 for each chromosome. Here, plot 1410 represents chromosome 1 of the patient, although site 106 may include a plot for some or all of the chromosomes for which data has been uploaded. Referring to plot 1408, this plot includes a potential region of interest 1412. As can be visually seen, this region indicates that the patient may have a chromosomal segment loss or gain at this particular location (here, in chromosome 15). Plot 1408 also includes a region 1414 that visually indicates that the patient's genome includes a Y chromosome—thus affirming that this patient is indeed male as indicated in information 902 above.

Figure 15:
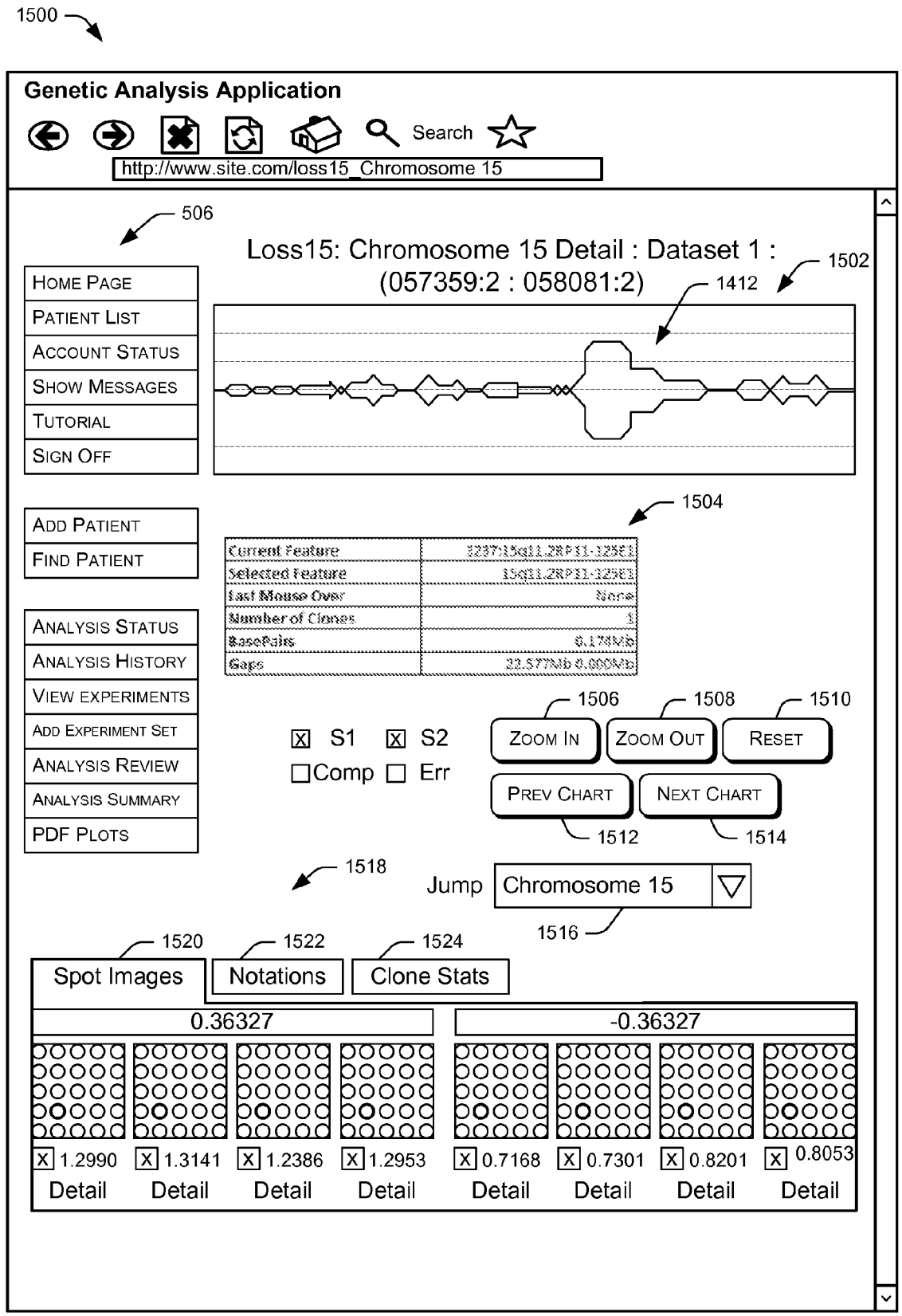
FIG. 15 illustrates yet another example page served by the site of FIG. 1. This example page includes a visual representation of a particular chromosome on the slide, as well as multiple visual representations of spot images of the slide.

FIG. 15 illustrates an example page 1500 served by site 106 after a user has selected a plot associated with an individual chromosome from page 1400. Here, the user has selected a plot 1502 associated with chromosome 15 of the patient. As illustrated, plot 1502 includes region 1412—previously seen as a region of interest in the plot of the patient's genome from page 1400. Plot 1502, however, provides the user with a closer view of region 1410 in order to help the user determine whether this region does indeed represent a chromosomal DNA gain or loss.

Page 1500 further includes information 1504, which indicates the current features being displayed, the currently selected feature, the location of the mouse over, the number of clones being examined, the size of the corresponding base pairs, and any gaps that exists between clones. Page 1500 may also include icons that allow the user to manipulate plot 1502. For instance, the user may zoom in or out on the chart by selecting icons 1506 and 1508, respectively. Selection of an icon 1510 allows the chart to be reset to the original configuration.

The user may also navigate to plots associated with other chromosomes of the patient. For instance, the user may choose to view the previous chart by selecting an icon 1512 or may choose to view the next chart by selecting an icon 1514. Conversely, the user may jump to any chromosome for which site 106 has created a plot with use of a drop-down menu 1516.

Figure 21:
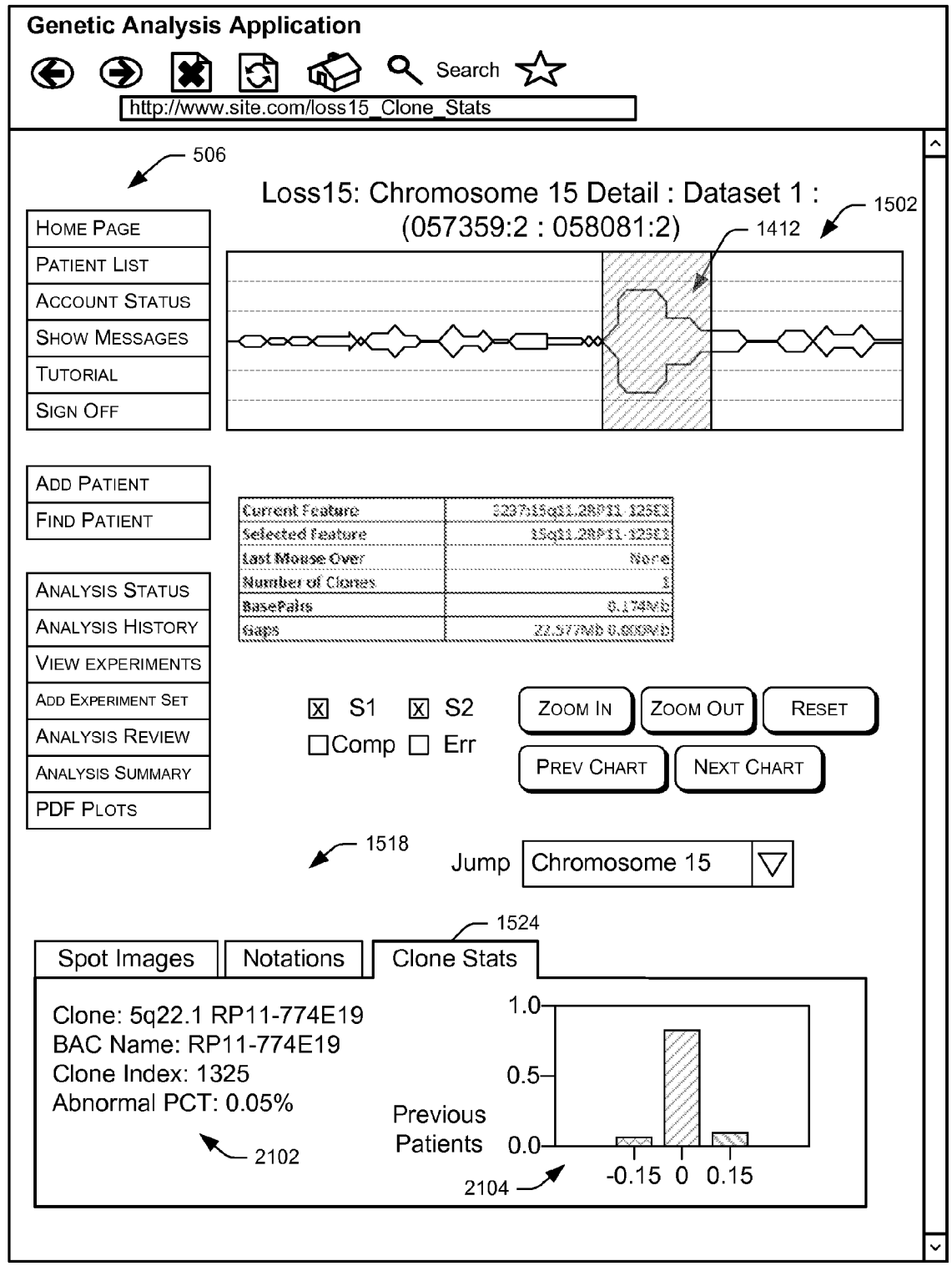
FIG. 21 illustrates yet another example page served by the site of FIG. 1. This example page includes the visual representation of the slide from FIG. 15, as well as statistics about previously-uploaded patient data. These statistics may allow a user to see if the uploaded data appears to be performing correctly or if the region is generally variable in terms of copy number.

Page 1500 further includes an area 1518 that includes three tabs that the viewing user may utilize. A tab 1520 ("Spot Images") includes visual representations of the spots on the slide from which the current plot has been created, and is discussed in detail immediately below. Next, a tab 1522 ("Notations") allows the user to annotate the information being viewed in plot 1502, and is discussed in detail below with reference to FIG. 16. Finally, a tab 1524 ("Clone Stats") allows the user to compare the currently-viewed data associated with the patient with data for multiple other patients at the same position in the genome. FIG. 21 and an accompanying discussion illustrate and describe tab 1524 in detail below.

As illustrated, tab 1520 may include spot images for both the first experiment and the reversed second experiment. Also as illustrated, each spot image may be reproduced such that tab 1520 includes multiple reproductions of the spots on the slide. For instance, page 1500 here illustrates that, for each experiment, tab 1520 includes four reproductions of a particular spot image. By reproducing and testing each area four times, the likelihood of a bad spot reproduction (that was not automatically filtered out by site 106) affecting the results is greatly decreased.

Furthermore, each of the reproductions is selectable and de-selectable by the user in order to choose whether or not data from that particular spot image should be used in the calculation of plot 1502 and the underlying statistics. Here, for instance, a check box is associated with each spot image, such that when the box is checked for a particular spot image, the calculations based on that spot image are used in the plot. When the box is unchecked, the calculations based on that image are not used in the plot.

Because each of these spot images is selectable and de-selectable, the user may visually analyze the quality of each image to determine whether or not he or she wishes to include that spot image in the calculations. For instance, the user may see that one or more of the reproductions of the spots are scratched, smudged, or have hybridized poorly. In response, the user may choose to de-select those one or more images. Genetic analysis application 116 will then exclude these de-selected images from the calculations and will recalculate any potential gain or loss at the particular location at issue in the chromosome.

In addition to providing visual representations of the spots, tab 1520 may also include a numerical representation of the calculated gain or loss for each spot image. In the illustrated implementation, a calculation of one represents a perfectly-balanced genetic region. Therefore, an amount over and under this number represents a degree of DNA gain or loss. At some threshold over and under this number, site 106 or the user determines that a loss or gain does indeed exist and should be researched. Furthermore and as illustrated, site 106 depicts a numerical value for each image spot.

In some instances, site 106 initially calculates a degree of gain or loss based on all of the four spot images and creates plot 1502 to represent this calculation. The user may then choose to de-select one or more of these images (e.g., because one of the spot images appears scratched). Site 106 may then recalculate a degree of gain or loss, with this recalculation including the selected spot images and excluding the de-selected ones.

Furthermore, the illustrated spot images may correspond to the currently-selected locations of plot 1502. That is, the user may select (e.g., with his or her mouse) a particular location on plot 1502. Tab 1520 will, in response, display spot images corresponding to that location. If the user selects another location in the plot, then tab 1520 may display spot images corresponding to the newly-selected location.

Figure 16:
FIG. 16 illustrates yet another example page served by the site of FIG. 1. This example page includes the visual representation of the slide from FIG. 15, as well as an area where a user may provide a notation for association with a selected region of the illustrated chromosome.

FIG. 16 illustrates an example page 1600 that appears when a user of page 1500 selects tab 1522. Tab 1522 allows the user to create a notation about a location in the illustrated plot 1502. For instance, a user may select (e.g., by dragging and dropping a cursor with his or her mouse or in any other suitable manner) a particular region on plot 1502. The user may then create a notation for association with this selected region. Therefore, when other users of application 116 compare their patient data against the currently-illustrated patient data, these other users may read the notation to better help these other users in diagnosing their patients. Additionally, the user who creates the notation may benefit from the notation by later accessing what he or she wrote.

As illustrated, tab 1522 includes a drop down menu that has auto-filled with the region or location selected in plot 1502. As such, this location indicated in the menu is the location that will be associated with the created notation. The user may change this location by altering the indicated location in the drop-down menu or by choosing a different region or location on plot 1502.

Tab 1522 also includes a drop-down menu entitled "Copy Number." The options may include copy loss and copy gain. Here, the menu indicates that the user has selected (or the site has suggested) that the currently-selected location in plot 1502 represents a copy loss. Finally, tab 1522 also includes a free-form text box in which the user may insert one or more comments about the selected region. Here, for instance, the user has inserted the comment "del(15)," meaning that this selection region of plot 1502 likely represents a loss in chromosome 15 of the patient.

Figure 17:
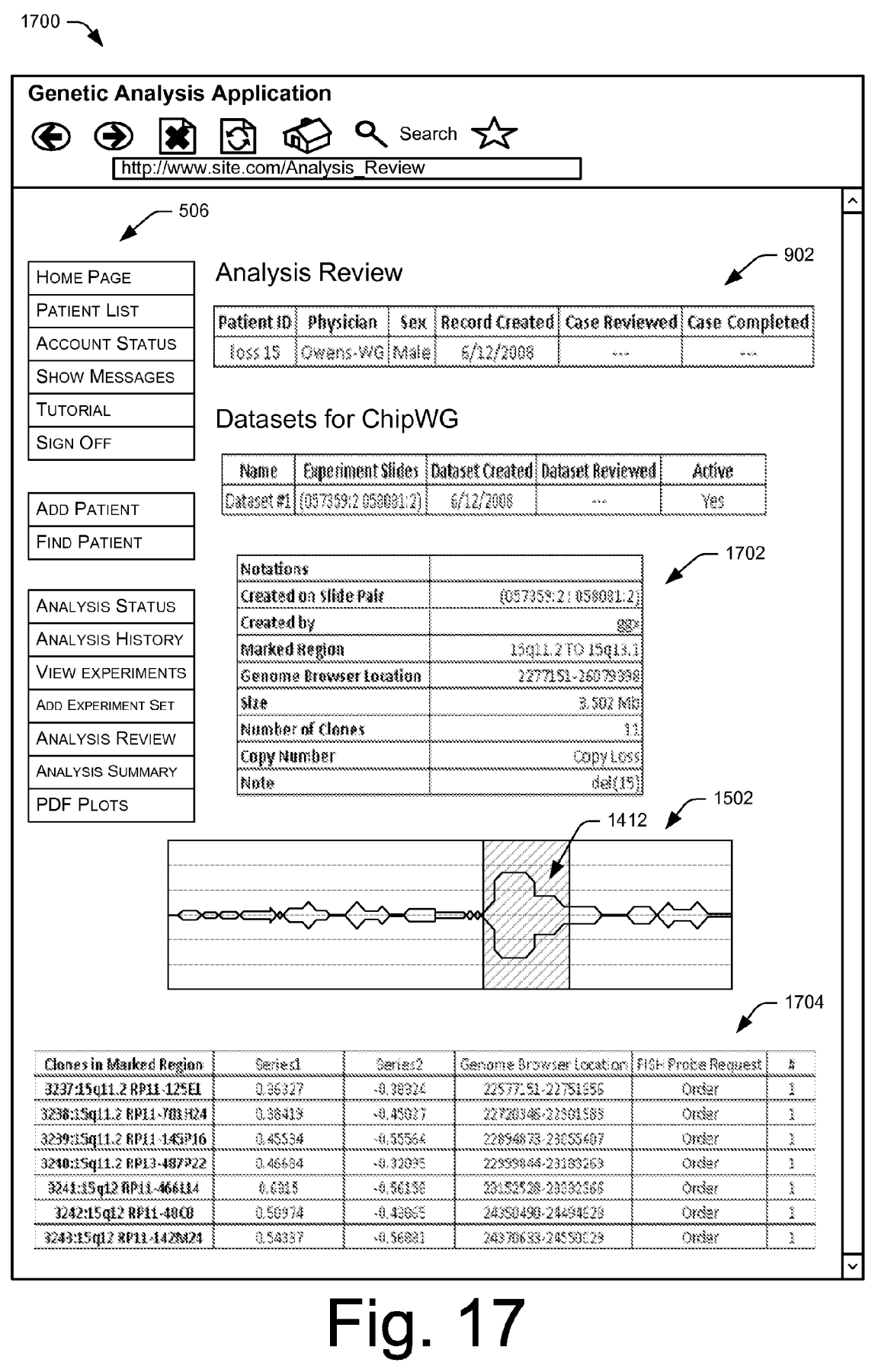

FIG. 17 illustrates an example page 1700 that site 106 may serve after the user has selected link 922 ("Analysis Review") from menu 506. Page 1700 includes information 1702 about the notation(s) completed by the user on page 1600. This information includes, for instance, the slide pair on which the notation was created, who created the notation, the "marked region" associated with the notation, this location in the genome browser, the size, the number of clones that the marked region includes, the copy number ("copy loss"), as well as the actual text or note provided by the user ("del(15)").

Page 1700 also includes plot 1502, as well as the highlighted region that is associated with the notation. Page 1700 further includes a list of the clones 1704 in the marked region along with an identification of where in the genome these clones occur. Furthermore, list 1704 allows the user to directly order one or more FISH probes for each of the clones in the highlighted region. That is, application 116 automatically determined the clones that are associated with the highlighted region 1412, automatically determined the location of these clones in the genome browser, and automatically provided the user the opportunity to choose to order some or all of the FISH probes for the clones determined to reside within the highlighted region. All of this allows the user to easily order one or more FISH probes to double-check the user's hypothesis that the patient associated with plot 1502 has a chromosomal DNA copy loss at region 1412.

Figure 18:
FIG. 18 illustrates yet another example page served by the site of FIG. 1. This example page includes an analysis summary of the patient data.

FIG. 18 illustrates an example page 1800 that site 106 may serve in response to the user selecting link 924 ("Analysis Summary") from menu 506. Page 1800 may include, in text form, information 1802 about the patient data and about the analysis provided by the user, such as the notation, the location of the notation, and the like. Because information 1802 is in text form, it may be easily copied and pasted into a written report of the user, if necessary.

Figure 19:
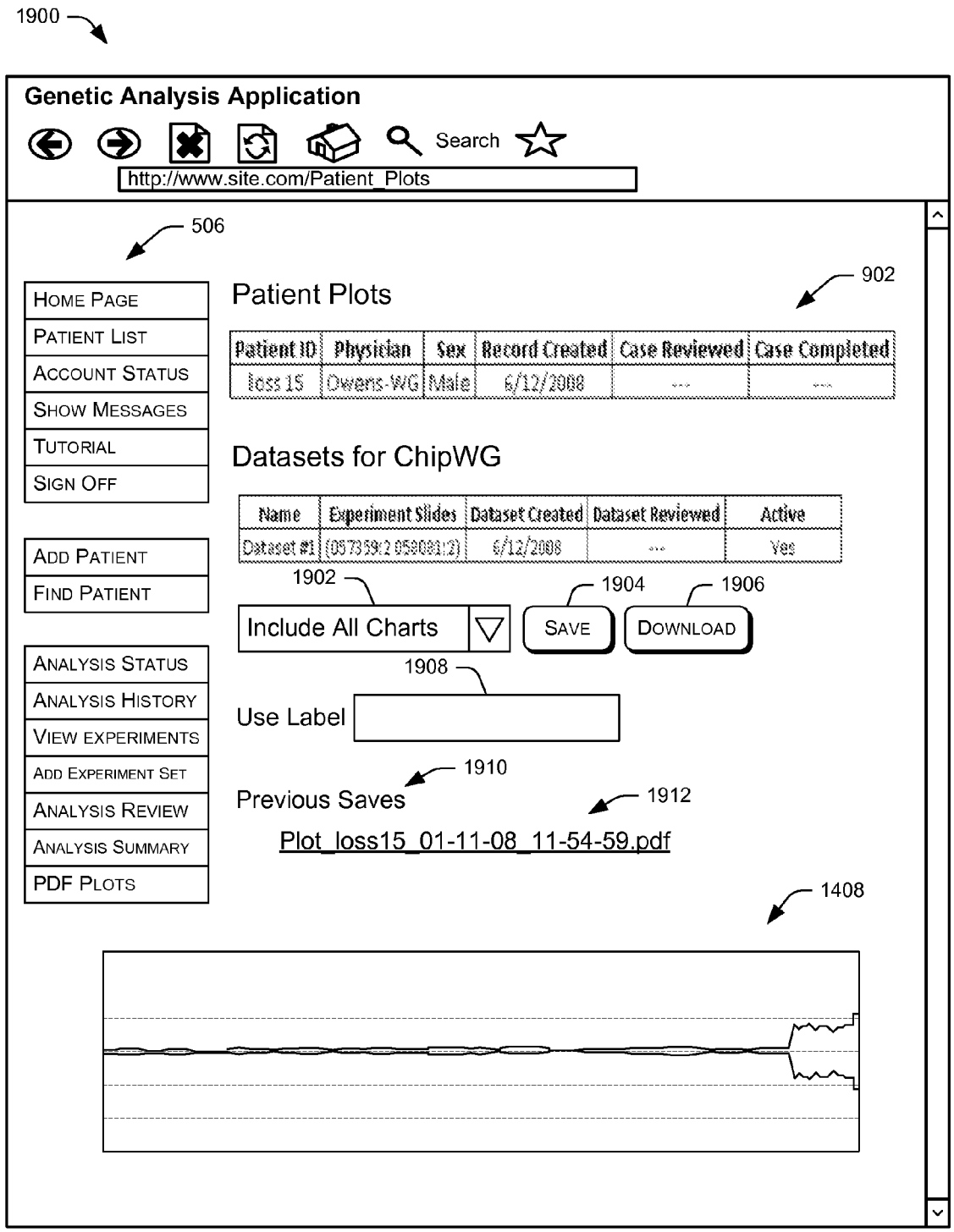
FIG. 19 illustrates yet another example page served by the site of FIG. 1. This example page includes a plot of the patient data, as well as previously-saved, patient-data plots.

FIG. 19 illustrates an example page 1900 that site 106 may serve in response to the user selecting link 926 ("PDF Plots") from menu 506. Page 1900 allows the user to create a PDF plot of the analysis, if needed, for saving to site 106 and/or for downloading to the user's local computing device. Page 1900 may also provide access to previously-saved plots.

As illustrated, page 1900 includes a drop-down menu 1902 that allows the user to select some or all charts from a list. For instance, the user may choose to save all of the charts corresponding to each chromosome, a chart of a particular chromosome, or a chart of the patient's whole genome (corresponding to plot 1408 discussed above). Page 1900 also includes an icon 1904 that, when selected, instructs application 116 to save the plot of the currently-analyzed data to site 106. Additionally or alternatively, the user may choose to download a PDF plot of the one or more plots via selection of an icon 1906 entitled "Download." If the user wishes to save the plot to site 106, then the user may label the chart by inserting a label into a text box 1908.

As discussed above, page 1900 may also include an area 1910 that lists PDF plots that the user has previously saved to site 106. Here, page 1900 indicates that the user has saved a single plot 1912 to site 106. Selection of plot 1912 may result in the appearance and/or download of the corresponding PDF plot.

Figure 20:
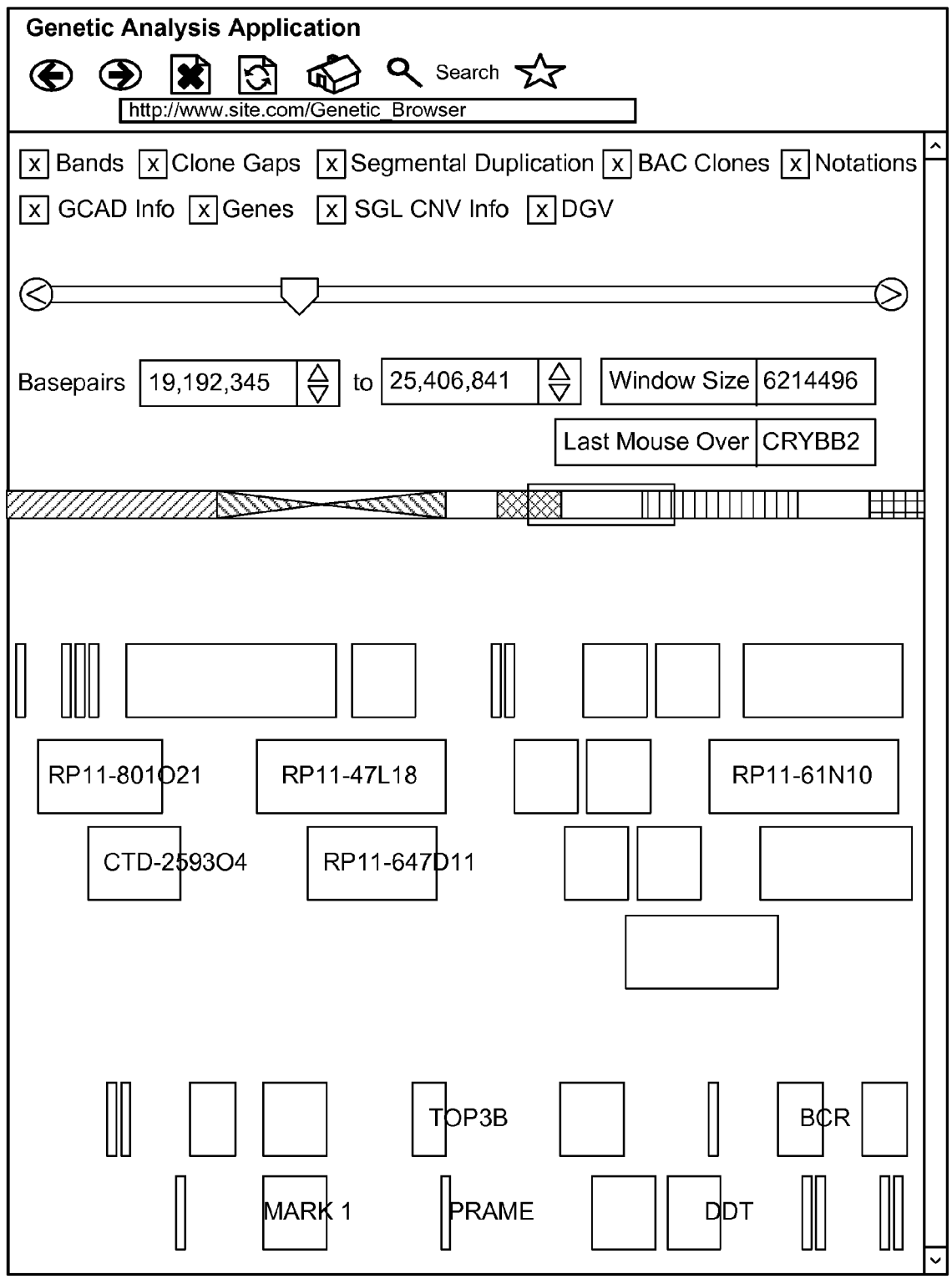
FIG. 20 illustrates yet another example page served by the site of FIG. 1. This example page comprises an interactive genome browser that may include information about a particular patient's uploaded data, as well as information about the human genome generally.

FIG. 20 illustrates another example page 2000 served by the site of FIG. 1. This example page comprises an interactive genome browser that may include information about a particular patient's uploaded data, as well as information about the human genome generally. For instance, page 2000 displays the layout of the uploaded BAC clones for the particular patient, the gap there between, coverage of the corresponding genes, the copy number variance that service provider site 106 has tracked for the specified location of the genome, information about copy number variance as provided by one or more public databases, and segmental duplications (i.e., low-copy repeats) in the human genome. Importantly, page 2000 may also show notations made by users of application 116 at corresponding locations. For instance, when a user views the genome browser at a location within chromosome 15, that user may see the notation made at chromosome 15 via page 1600.

FIG. 21 illustrates an example page 2100 that appears when the user of page 1500 selects tab 1524. This page includes plot 1502 of chromosome 15 of the patient, as well as statistics about previously-uploaded patient data at the highlighted region. As illustrated, tab 1524 (entitled "Clone Stats") illustrates statistics for the selected region of the genome as calculated by site 106 based on previously-uploaded patient data. Tab 1524 here includes information 2102 about the clone stats, including an identification of the one or more clones on which the statistics are based, the corresponding BAC name(s), the corresponding clone index(es), and the abnormal percentage that service provider site 106 has seen at this site based on the previously-uploaded patient data.

Tab 1524 also includes a visual representation 2104 of these statistics. Here, visual representation 2104 comprises a bar graph that illustrates a percentage of patients that have exhibited chromosomal segment loss at this location, a percentage of patients that have exhibited chromosomal segment gain at this location, and a percentage of patients that have neither exhibited loss nor gain. As information 2102 illustrates, in the illustrated implementation patients whose data has been previously uploaded have shown either gain or loss about 0.05% of the time.

With this information, users can determine whether a particular DNA copy loss or gain is commonly found (known as copy number variation), or whether such an abnormality is rare. In the former instances, then a user, such as a doctor or clinician, may determine that his or her patient's loss or gain may be a normal copy gain or loss, as site 106 indicates that such a loss or gain is commonly found. Conversely, if the latter instances, the doctor or clinician may take very seriously a DNA copy loss or gain in a location where such abnormalities are seldom found. Furthermore, in some implementations, site 106 may provide notations in addition to the statistics. For instance, site 106 could indicate that a particular loss or gain is "commonly found" and "not associated with a genetic syndrome." Site 106 could also indicate that a particular loss or gain is "mildly" or "strongly associated with" a particular genetic syndrome, such as autism or the like. Users 102(1)-(N) and/or representatives 128 of service provider 128 may provide these types of notations to site 106. This information may prove very useful to users who are analyzing patient data that shows a DNA copy loss or gain at a location having such a notation.

Illustrative Processes

Figure 22:
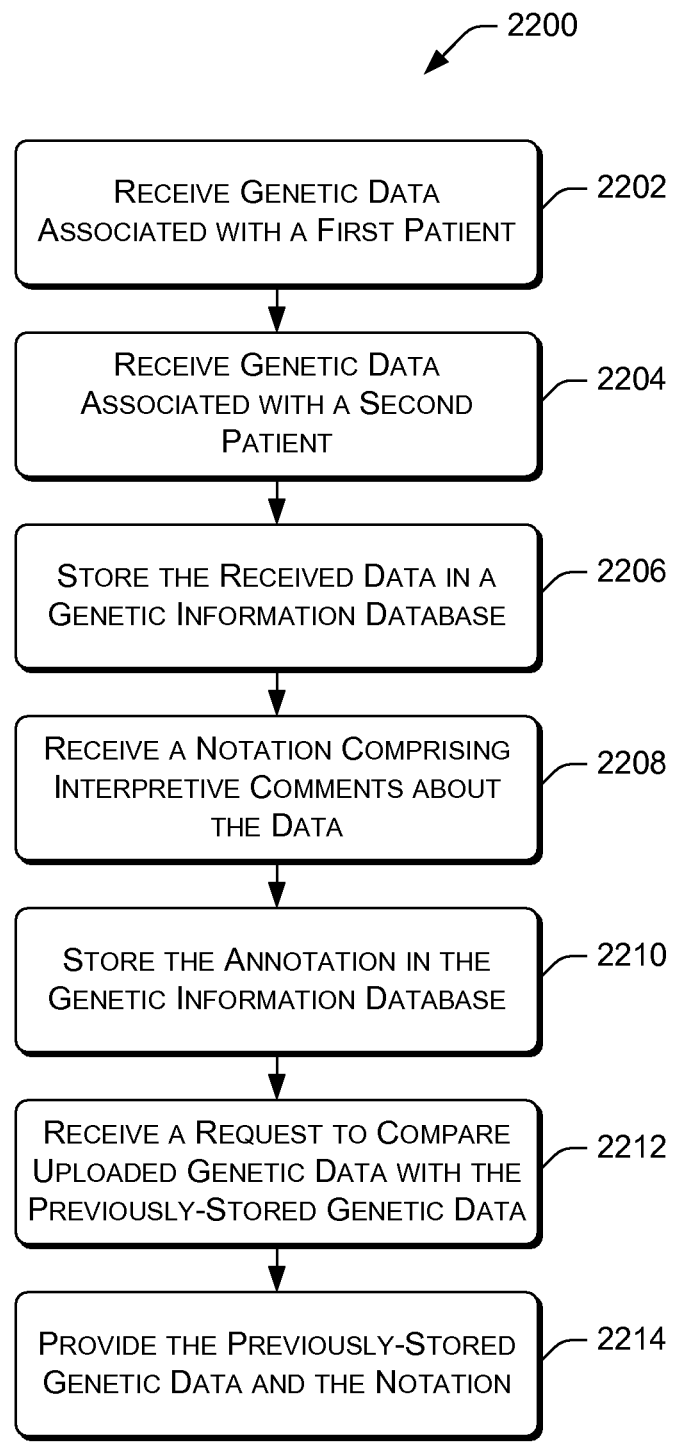
FIG. 22 illustrates a flow diagram of an example process that includes receiving genetic data from multiple patients in multiple locations, the genetic data for comparison to data uploaded by other users.
Figure 23:
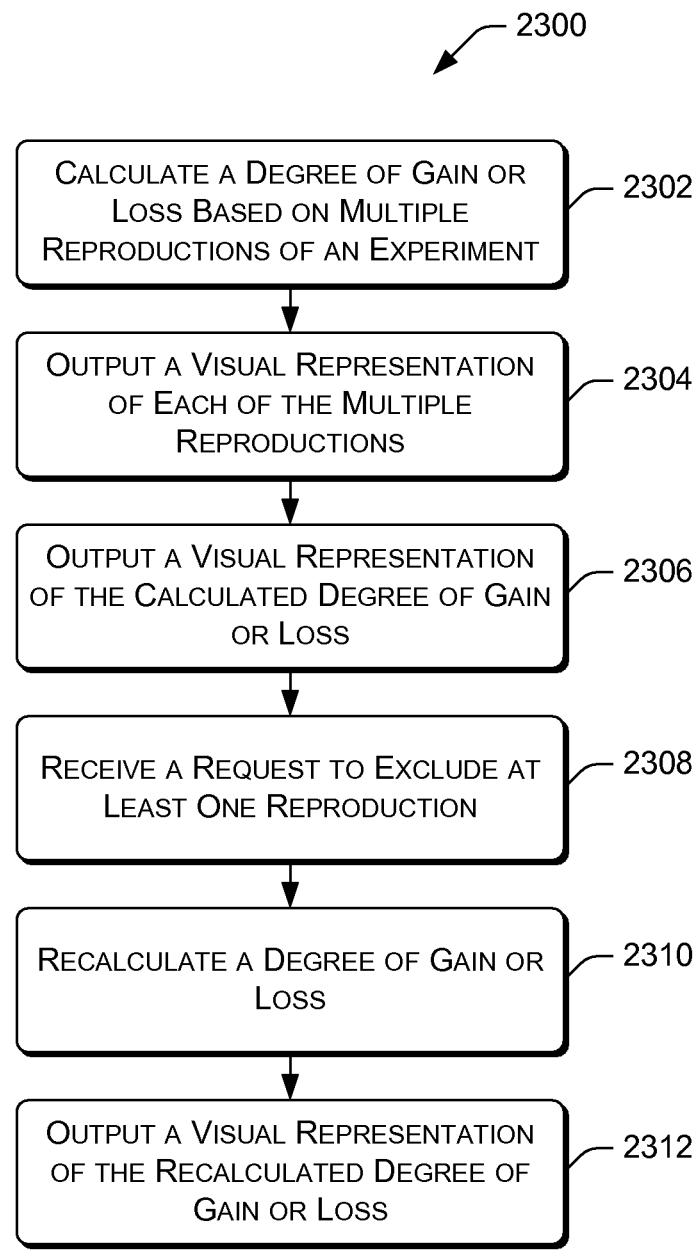
FIG. 23 illustrates a flow diagram of an example process that includes calculating a degree of chromosomal DNA copy loss or gain, receiving a request to exclude at least one source on which the calculation was based, and recalculating a degree of chromosomal segment loss or gain without reference to the excluded source(s).
Figure 24:
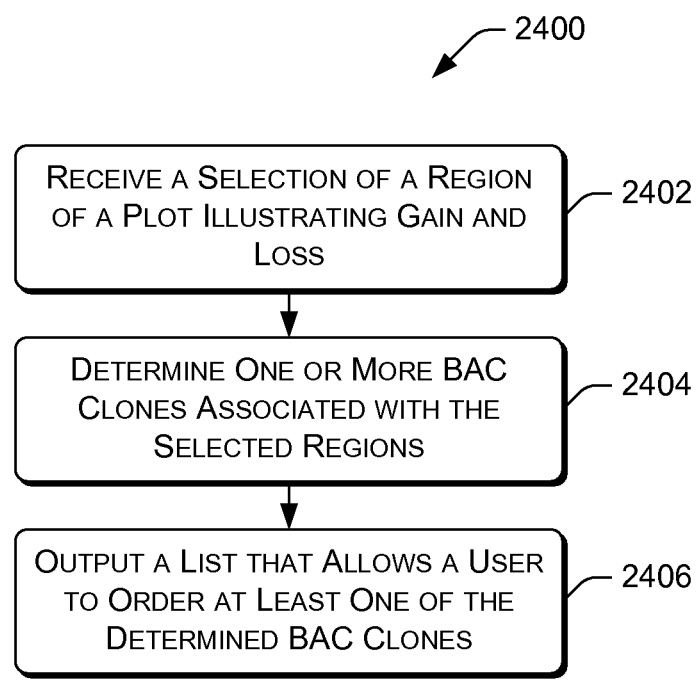
FIG. 24 illustrates a flow diagram of an example process for outputting a list from which a user may order desired FISH probes.

FIGS. 22-24 illustrate example processes 2200, 2300 and 2400 for implementing the techniques discussed above. Each of these processes is illustrated as a collection of blocks in a logical flow graph, which represent a sequence of operations that can be implemented in hardware, software, or a combination thereof. In the context of software, the blocks represent computer-executable instructions that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the process.

While processes 2200, 2300 and 2400 may be implemented in architecture 100 of FIG. 1, these processes may also be implemented in a varying array of other architectures, environments and contexts.

Process 2200 includes operation 2202, which represents receiving genetic data associated with a first patient from a first user at a first location. For instance, site 106 may receive patient data 126(1) from user 102(1) of FIG. 1. Next, operation 2204 represents receiving genetic data associated with a second patient form a second user at a second location. For instance, site 106 may receive patient data 126(2) from user 102(2). Both of the received pieces of genetic data may then be stored in a genetic information database, such as database 114, for use by another user in comparing this stored data with genetic data associated with another patient. For instance, user 102(N) may use this stored genetic data to compare with patient data 126(N). As such, user 102(N) may be able to better diagnosis his or her patient.

Operation 2208, meanwhile, receives a notation comprising interpretive comments about one or both pieces of the genetic data. For instance, user 102(1) may have provided a notation via tab 1522 of page 1600. At operation 2210, this notation is stored in, for example, genetic information database 114. Next, operation 2212 receives a request to compare currently-uploaded genetic data with previously-stored genetic data, such as the data provided by users 102(1) and 102(2). In response, operation 2214 provides the previously-stored genetic data as well as the created notation. For instance, this information may be provided on a user interface via a page served by site 106.

FIG. 23 illustrates process 2300, which includes calculating a degree of DNA copy loss or gain based on one or more reproductions of a slide at operation 2302. For instance, this calculation may be based on the spot images shown in FIG. 15. Next, operation 2304 outputs a visual representation of each of the multiple slides, while operation 2306 outputs a visual representation (e.g., a plot) of the calculated degree of loss or gain. Next, operation 2308 receives a request (e.g., via the un-checking of the illustrated checkboxes of FIG. 15 or otherwise) to exclude at least one reproduction from the calculation. In response, operation 2310 recalculates a degree of loss or gain. Finally, operation 2312 outputs a visual representation (e.g., a plot) of the recalculated degree of loss or gain.

FIG. 24 illustrates process 2400, and includes receiving, from a user and at operation 2402, a selection of a region of a plot that illustrates chromosomal loss or gain. For instance, the user may select this region by dragging and dropping his or her cursor with use of a mouse, by numerically specifying a region, or in any other suitable manner. Next, responsive to the receiving of the selection, operation 2404 determines one or more bacterial artificial chromosome (BAC) clones that are associated with the selected region. For instance, this operation may determine which clones reside within the selected region. Finally, operation 2406 outputs, to the user, a list of the determined one or more BAC clones, the list allowing the user to order a fluorescent in situ hybridization (FISH) probe for at least one of the determined one or more BAC clones. For instance, a list such as list 1704 may be output to the user in order to allow the user to order one or more of each listed BAC clone.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A server system, comprising:
one or more processors;
memory; and
a web-based genetic analysis application, stored in the memory and executable on the one or more processors, configured to:
allow a user to upload genetic data associated with a patient, and
compare the uploaded genetic data with genetic data associated with multiple other patients that has been previously uploaded by multiple other users of the web-based genetic analysis application, the genetic data associated with the patient and the genetic data associated with the multiple other patients comprising indications of chromosomal segment gain or loss for a respective patient, wherein the comparing of the uploaded genetic data with the genetic data associated with the multiple other patients comprises comparing the chromosomal segment gain or loss of the patient with statistics indicating a frequency of occurrence of the chromosomal segment gain or loss among the multiple other patients.

2. A server system as recited in claim 1, wherein the web-based genetic analysis application is further configured to allow the user to annotate the uploaded genetic data for use by other users in future analysis of the uploaded genetic data.

3. A server system as recited in claim 1, wherein the web-based genetic analysis application is further configured to allow the user to upload interpretive comments regarding the uploaded genetic data for use by other users in future analysis of the uploaded genetic data.

4. A server system as recited in claim 1, wherein the chromosomal segment gain or loss comprises gain or loss of at least one chromosome or chromosome segment.

5. One or more computing devices, comprising:
one or more processors;
memory;
a genetic information database, stored in the memory and operable on the one or more processors, configured to store genetic data associated with multiple patients, the genetic data including chromosome information indicating chromosomal segment gain or loss associated with one or more chromosomal segments and one or more patients; and
an application, stored in the memory and operable on the one or more processors, configured to:

receive the genetic data from multiple different users at multiple different locations, aggregate the genetic data to calculate statistic data of the chromosomal segment gain or loss associated with a chromosomal segment of the one or more chromosomal segments, and associate the statistic data with the one or more patients, wherein the genetic information database comprises indications that frequently occurring chromosomal segment gain or loss is frequently found as normal copy number variant gain or loss.

6. One or more computing devices as recited in claim 5, wherein the genetic data is for comparison to particular genetic data associated with particular patients.

7. One or more computing devices as recited in claim 5, wherein the genetic information database is further configured to store notations associated with one or more pieces of the genetic data, the notations having been made by a first user of the genetic information database and for use by another user of the genetic information database.

8. One or more computing devices as recited in claim 5, wherein the genetic information database is further configured to store interpretative comments regarding the chromosomal segment gain or loss of respective patients of the multiple patients.

9. One or more computing devices as recited in claim 8, wherein the interpretative comments comprise indications that particular chromosomal segment gain or loss is associated with particular genetic syndromes.

10. One or more computing devices as recited in claim 5, wherein the chromosomal segment gain or loss comprises gain or loss of at least one chromosome or chromosome segment.

11. One or more non-transitory computer-readable media storing computer-executable instructions that, when executed on one or more processors, perform acts comprising:
receiving genetic data associated with a first patient from a first user at a first location;
receiving genetic data associated with a second patient from a second user at a second location;
filtering the genetic data associated with a first patient and genetic data associated with a second patient to obtain filtered genetic data that identifies gain or loss of one or more chromosomal regions that is associated with one or more genetic disorders;
storing the filtered genetic data in a genetic information database that is accessible by multiple other users; and
enabling at least one of the first user or the second user to compare the filtered genetic data with genetic data associated with multiple other patients to obtain statistics indicating a frequency of occurrence of the chromosomal segment gain or loss among the multiple other patients.

12. One or more non-transitory computer-readable media as recited in 11, wherein the genetic information database is accessible by the multiple other users via a web-based application.

13. One or more non-transitory computer-readable media as recited in 11, wherein the gain or loss of one or more chromosomal regions comprises gain or loss of at least one chromosome or chromosome segment.

14. One or more non-transitory computer-readable media as recited in 11, further comprising:
receiving a notation from a third user at a third location, the notation comprising interpretative comments about the filtered genetic data that is associated with the first patient or the second patient; and storing the received notation in association the filtered genetic data that is associated with the first patient or the second patient.

15. One or more non-transitory computer-readable media as recited in 14, wherein the genetic information database is accessible by the multiple other users via a web-based application, and further comprising:
receiving a request to compare uploaded genetic data with the filtered genetic data that is associated with the first patient and the second patient; and
responsive to the receiving of the request, providing: (i) the filtered genetic data, and (ii) the received notation that is associated with the filtered genetic data associated with the first patient or the second patient.

16. One or more computing devices, comprising:
one or more processors; and
one or more computer-readable media storing computer-executable instructions that, when executed on the one or more processors, render a graphical user interface, the graphical user interface comprising:
a first area comprising a visual representation of a particular portion of genetic data associated with a patient; and
a second area comprising analysis of the particular portion of genetic data, the analysis of the particular portion being based on genetic data from multiple other patients, the particular portion of genetic data comprising one or more chromosomes, and the visual representation of the one or more chromosomes comprising a plot of the one or more chromosomes that indicates chromosomal segment gain or loss of the patient, wherein the analysis of the particular portion that is based on genetic data from the multiple other patients comprises a statistical breakdown of copy gain and loss previously seen in the multiple other patients in the particular portion of the genetic data.

17. One or more computing devices as recited in claim 16, wherein the particular portion of genetic data comprises a particular chromosome of the human genome.

18. One or more computing devices as recited in claim 16, further comprising a third area that, when selected, allows a user to create a notation for association with the particular portion of the genetic data associated with the patient, the created notation for use by other users in analyzing: (i) the particular portion of the genetic data associated with the patient, or (ii) the particular portion of the genetic data associated with another patient.

19. One or more computing devices as recited in claim 16, further comprising a third area that, when selected, displays spot images of slides from which the visual representation of the particular portion of the genetic data associated with the patient was created.

20. One or more computing devices as recited in claim 19, wherein the third area includes multiple reproductions of each spot image, and wherein the third area includes an icon associated with each reproduction of each spot image, wherein de-selection of the icon of a reproduction by a user removes the corresponding deselected spot image from calculations used in creating the visual representation of the particular portion of the genetic data associated with the patient.

21. One or more computing devices as recited in claim 16, wherein the chromosomal segment gain or loss comprises gain and/or loss of at least one chromosome or chromosome segment.

22. One or more computing devices, comprising:
one or more processors;
memory; and a web-based genetic analysis application, stored in the memory and executable on the one or more processors, the web-based genetic analysis application comprising:
  a genetic analysis engine configured to: (i) receive, over a network, genetic data associated with multiple patients, and (ii) analyze the received genetic data to calculate statistics regarding chromosomal segment gain or loss of the multiple patients; and
  a user interface component configured to output, over the network, a user interface that includes: (i) a representation of genetic data for a particular patient, and (ii) the calculated statistics regarding the chromosomal segment gain or loss of the multiple patients, wherein the calculated statistics regarding the chromosomal segment gain or loss of the multiple patients comprises a chart representing a frequency with which a loss or a gain is found in a particular region of a chromosome.

23. One or more computing devices as recited in claim 22, wherein the genetic analysis engine is further configured to receive interpretive comments regarding the chromosomal segment gain or loss of the multiple patients or regarding the segment gain or loss of a single particular patient.

24. One or more computing devices as recited in claim 23, wherein the interpretive comments comprise an indication that chromosomal segment gain or loss of a particular chromosome is common among the multiple patients.

25. One or more computing devices as recited in claim 23, wherein the interpretive comments comprise an indication that chromosomal segment gain or loss of a particular chromosome is associated with a genetic syndrome among the multiple patients.

26. One or more computing devices as recited in claim 23, wherein the user interface component is further configured to output the interpretive comments for display to a user accessing the web-based genetic analysis application over the network.

27. One or more computing devices as recited in claim 22, wherein the user interface component is further configured to output a user interface that includes: (i) a representation of genetic data for a particular patient, and (ii) an area to create a notation for association with the genetic data.

28. One or more computing devices as recited in claim 27, wherein the created notation is accessible by other users when analyzing genetic data that includes the genetic data for the particular patient.

29. One or more computing devices as recited in claim 22, wherein the user interface component is further configured to output a user interface that includes: (i) a representation of genetic data for a particular patient, and (ii) spot images from slides from which the representation of the genetic data for the particular patient was created.

30. One or more computing devices as recited in claim 29, wherein the user interface includes multiple reproductions of each spot image, and wherein the user interface further includes an icon associated with each reproduction of each spot image, wherein de-selection of the icon of a reproduction by a user removes the corresponding deselected spot image from calculations used in creating the representation of the genetic data for the particular patient.

31. One or more computing devices as recited in claim 22, wherein the chromosomal segment gain or loss comprises gain or loss of at least one chromosome or chromosome segment.

32. One or more non-transitory computer-readable storage media storing computer-executable instructions that, when executed on one or more processors, perform acts comprising:
  calculating a degree of chromosomal segment gain or loss for a patient based on multiple reproductions of a portion of a genetic testing experiment;
  receiving a request to exclude at least one of the multiple reproductions of the portion of the genetic testing experiment in a recalculation of the degree of the chromosomal segment gain or loss; and
  responsive to the receiving of the request, recalculating a degree of the chromosomal segment gain or loss for the patient, the recalculation excluding the at least one of the multiple reproductions of the portion of the genetic testing experiment, the degree of the chromosomal segment gain or loss for the patient indicating a frequency of occurrence of the chromosomal segment gain or loss of the patient among multiple other patients.

33. One or more non-transitory computer-readable storage media as recited in claim 32, wherein the genetic testing experiment comprises an array comparative genomic hybridization (CGH) slide or a CGH slide.

34. One or more non-transitory computer-readable storage media as recited in claim 32, further storing computer-executable instructions that, when executed on the one or more processors, perform an act comprising outputting a visual representation of each of the multiple reproductions of the portion of the genetic testing experiment.

35. One or more non-transitory computer-readable storage media as recited in claim 34, wherein the visual representation of the reproduction marked for exclusion indicates that the reproduction has been damaged.

36. One or more non-transitory computer-readable storage media as recited in claim 32, further storing computer-executable instructions that, when executed on the one or more processors, perform acts comprising:
  prior to the recalculation, outputting a visual representation of the calculated degree of chromosome or chromosome segment loss or gain; and
  after the recalculation, outputting a visual representation of the recalculated degree of chromosome or chromosome segment loss or gain.

37. One or more non-transitory computer-readable storage media as recited in claim 36, wherein the visual representations each comprise a plot of chromosomal segment gain or loss of a particular chromosome associated with the portion of the genetic testing experiment.

38. One or more computer-readable storage media as recited in claim 32, wherein the chromosomal segment gain or loss comprises gain or loss of at least one chromosome or chromosome segment.

39. One or more computing devices, comprising:
  one or more processors; and
  one or more computer-readable media storing computer-executable instructions that, when executed on the one or more processors, render a graphical user interface, the graphical user interface comprising:
    a first area comprising a visual representation of a particular portion of genetic data associated with a patient; and
    a second area comprising a reproduction of a portion of a genetic testing experiment that carries the genetic data associated with the patient from which the visual representation was created, the particular portion of genetic data comprising one or more chromosomes, and the visual representation of the one or more chromosomes comprising a plot of the one or more chromosomes that indicates chromosomal segment gain or loss of the patient, wherein the second area comprises multiple reproductions of a same location of the genetic testing experiment, the particular portion of genetic data comprises one or more chromosomes;

the visual representation of the one or more chromosomes comprises a plot of the one or more chromosomes that indicates the chromosomal segment pain or loss of the patient;

each of the multiple reproductions of the same location of the genetic testing experiment are selectable and de-selectable by a user; and the plot of the one or more chromosomes that indicates the chromosomal segment gain or loss of the patient changes based on which of the multiple reproductions are selected and which of the multiple reproductions are de-selected.

40. One or more computing devices as recited in claim 39, wherein the genetic testing experiment comprises an array comparative genomic hybridization (CGH) slide or a CGH slide.

41. One or more computing devices as recited in claim 39, wherein the particular portion of genetic data comprises a particular chromosome of the human genome.

42. One or more computing devices as recited in claim 39, wherein the visual representation of the particular portion of the genetic data associated with the patient is selectable at different locations by the user, and wherein the second area displays a reproduction of a portion of the genetic testing experiment that corresponds to the selected location of the visual representation.

43. One or more computing devices as recited in claim 39, further comprising a third area that, when selected, allows a user to create a notation for association with the particular portion of the genetic data associated with the patient, the created notation for use by other users in analyzing: (i) the particular portion of the genetic data associated with the patient, or (ii) the particular portion of the genetic data associated with another patient.

44. One or more computing devices as recited in claim 39, further comprising a third area comprising analysis of the particular portion of genetic data, the analysis of the particular portion being based on genetic data from multiple other patients.

45. One or more computing devices as recited in claim 44, wherein the analysis of the particular portion that is based on genetic data from the multiple other patients comprises a statistical breakdown of copy gain and loss previously seen in the multiple other patients in the particular portion of the genetic data.

46. One or more computing devices as recited in claim 39, wherein the chromosomal segment gain or loss comprises gain or loss of at least one chromosome or chromosome segment.

47. One or more non-transitory computer-readable media storing computer-executable instructions that, when executed on one or more processors, perform acts comprising:

receiving, from a user, a selection of a region of a plot that illustrates chromosomal segment gain or loss;

responsive to the receiving of the selection, determining one or more bacterial artificial chromosome (BAC) clones that are associated with the selected region; and outputting a list of the determined one or more BAC clones to instruct the user to order a fluorescence in situ hybridization (FISH) probe for at least one of the determined one or more BAC clones.

48. One or more non-transitory computer-readable media as recited in claim 47, wherein the user selects the region by dragging and dropping a cursor on the plot that illustrates the chromosomal segment gain or loss.

49. One or more non-transitory computer-readable media as recited in claim 47, wherein the plot that illustrates the chromosomal segment gain or loss is a plot of a single chromosome.

50. One or more non-transitory computer-readable media as recited in claim 47, wherein the determined one or more BAC clones comprises at least a majority of the BAC clones that reside within the selected region.

51. One or more non-transitory computer-readable media as recited in claim 47, wherein the outputted list allows the user to order a FISH probe for each of the determined one or more BAC clones.

52. One or more non-transitory computer-readable media as recited in claim 47, wherein the one or more determined BAC clones comprises each BAC clone that resides within the selected region, and wherein the outputted list allows the user to order a FISH probe for each BAC clone that resides within the selected region.

53. One or more non-transitory computer-readable media as recited in claim 47, wherein the chromosomal segment gain or loss comprises gain or loss of at least one chromosome or chromosome segment.

* * * * *